(12) United States Patent
Veedu

(10) Patent No.: US 11,786,611 B2
(45) Date of Patent: Oct. 17, 2023

(54) METHODS FOR TREATING VEGF-RELATED CONDITIONS

(71) Applicant: Murdoch University, Murdoch (AU)

(72) Inventor: Rakesh Veedu, Murdoch (AU)

(73) Assignee: Murdoch University, Murdoch (AU)

( * ) Notice: Subject to any disclaimer, the term of this patent is extended or adjusted under 35 U.S.C. 154(b) by 325 days.

(21) Appl. No.: 16/982,704

(22) PCT Filed: May 10, 2019

(86) PCT No.: PCT/AU2019/050438
§ 371 (c)(1),
(2) Date: Sep. 21, 2020

(87) PCT Pub. No.: WO2019/217997
PCT Pub. Date: Nov. 21, 2019

(65) Prior Publication Data
US 2022/0241435 A1 Aug. 4, 2022

(30) Foreign Application Priority Data

May 14, 2018 (AU) .................. 2018901653

(51) Int. Cl.
A61K 48/00 (2006.01)
C12N 15/113 (2010.01)
A61K 31/7105 (2006.01)

(52) U.S. Cl.
CPC ...... *A61K 48/0066* (2013.01); *A61K 31/7105* (2013.01); *C12N 15/1136* (2013.01);
(Continued)

(58) Field of Classification Search
CPC ............ A61K 48/0066; A61K 31/7105; C12N 15/1136; C12N 2310/11; C12N 2310/314;
(Continued)

(56) References Cited

U.S. PATENT DOCUMENTS 9,920,322 B2 * 3/2018 Collard .............. C12N 15/1136
10,525,070 B2 * 1/2020 Andrews .............. A61K 31/706
(Continued)

FOREIGN PATENT DOCUMENTS

WO WO 2001/052904 7/2001
WO WO 2008/045576 4/2008
(Continued)

OTHER PUBLICATIONS

Catena et al., Increased expression of $VEGF_{121}/VEGF_{165-189}$ ratio results in a significant enhancement of human prostate tumor angiogenesis, International Journal of Cancer, vol. 120(10): 2096-2109, May 2007.
(Continued)

*Primary Examiner* — Terra C Gibbs
(74) *Attorney, Agent, or Firm* — Howson & Howson LLP; Colleen M. Schaller; Francis J. Coffey

(57) ABSTRACT

An isolated or purified antisense oligonucleotide targeted to a nucleic acid molecule encoding vascular endothelial growth factor A (VEGF-A) pre-mRNA, wherein the antisense oligonucleotide has a nucleobase sequence selected from the list comprising SEQ ID NO: 1 to SEQ ID NO: 22 which has a modified backbone structure and sequences with at least 95% sequence identity to SEQ ID NO: 1-22 which have a modified backbone structure, and wherein the antisense oligonucleotide inhibits the expression of human VEGF-A.

16 Claims, 10 Drawing Sheets

Specification includes a Sequence Listing.

(52) U.S. Cl.
CPC .... *C12N 2310/11* (2013.01); *C12N 2310/314* (2013.01); *C12N 2310/3233* (2013.01); *C12N 2320/33* (2013.01); *C12N 2320/51* (2013.01)

(58) Field of Classification Search
CPC ........ C12N 2310/3233; C12N 2310/33; C12N 2310/51
See application file for complete search history.

(56) References Cited

U.S. PATENT DOCUMENTS

| | | | | |
|---|---|---|---|---|
| 10,660,922 | B2* | 5/2020 | Stewart | C12N 5/0691 |
| 2002/0165174 | A1* | 11/2002 | Gill | C12N 15/1136 514/44 A |
| 2005/0244851 | A1 | 11/2005 | Blume et al. | |
| 2008/0286866 | A1* | 11/2008 | Quay | C12N 15/1136 435/375 |
| 2010/0105134 | A1 | 4/2010 | Quay et al. | |
| 2010/0298411 | A1 | 11/2010 | Kubo et al. | |
| 2011/0034545 | A1* | 2/2011 | Kubo | A61P 35/00 435/325 |

FOREIGN PATENT DOCUMENTS

| | | |
|---|---|---|
| WO | WO 2008/110777 | 9/2008 |
| WO | WO 2011/139710 | 11/2011 |

OTHER PUBLICATIONS

International Search Report and Written Opinion issued on International Patent Application No. PCT/AU2019/050438, dated Jun. 7, 2019.

* cited by examiner

SEQUENCE LISTING

```
<160> NUMBER OF SEQ ID NOS: 29

<210> SEQ ID NO 1
<211> LENGTH: 25
<212> TYPE: RNA
<213> ORGANISM: Artificial Sequence
<220> FEATURE:
<223> OTHER INFORMATION: synthetic construct

<400> SEQUENCE: 1
gccugggacc acugaggaca gaaag                                                25

<210> SEQ ID NO 2
<211> LENGTH: 25
<212> TYPE: RNA
<213> ORGANISM: Artificial Sequence
<220> FEATURE:
<223> OTHER INFORMATION: synthetic construct

<400> SEQUENCE: 2
```

-continued uccuucugcc augggugcag ccugg                                          25

<210> SEQ ID NO 3
<211> LENGTH: 25
<212> TYPE: RNA
<213> ORGANISM: Artificial Sequence
<220> FEATURE:
<223> OTHER INFORMATION: synthetic construct

<400> SEQUENCE: 3
gaugauucug cccuccuccu ucugc                                          25

<210> SEQ ID NO 4
<211> LENGTH: 25
<212> TYPE: RNA
<213> ORGANISM: Artificial Sequence
<220> FEATURE:
<223> OTHER INFORMATION: synthetic construct

<400> SEQUENCE: 4
acagccaggg ggacucaccu ucgug                                          25

<210> SEQ ID NO 5
<211> LENGTH: 25
<212> TYPE: RNA
<213> ORGANISM: Artificial Sequence
<220> FEATURE:
<223> OTHER INFORMATION: synthetic construct

<400> SEQUENCE: 5
gaacuucacc acugcaugag aggcg                                          25

<210> SEQ ID NO 6
<211> LENGTH: 25
<212> TYPE: RNA
<213> ORGANISM: Artificial Sequence
<220> FEATURE:
<223> OTHER INFORMATION: synthetic construct

<400> SEQUENCE: 6
gcugcgcuga uagacaucca ugaac                                          25

<210> SEQ ID NO 7
<211> LENGTH: 25
<212> TYPE: RNA
<213> ORGANISM: Artificial Sequence
<220> FEATURE:
<223> OTHER INFORMATION: synthetic construct

<400> SEQUENCE: 7
cucgauugga uggcaguagc ugcgc                                          25

<210> SEQ ID NO 8
<211> LENGTH: 25
<212> TYPE: RNA
<213> ORGANISM: Artificial Sequence
<220> FEATURE:
<223> OTHER INFORMATION: synthetic construct

<400> SEQUENCE: 8
auguccacca gggucucgau uggau                                          25

<210> SEQ ID NO 9
<211> LENGTH: 25
<212> TYPE: RNA
<213> ORGANISM: Artificial Sequence

```
<220> FEATURE:
<223> OTHER INFORMATION: synthetic construct

<400> SEQUENCE: 9
caggguacuc cuggaagaug uccac                                              25

<210> SEQ ID NO 10
<211> LENGTH: 25
<212> TYPE: RNA
<213> ORGANISM: Artificial Sequence
<220> FEATURE:
<223> OTHER INFORMATION: synthetic construct

<400> SEQUENCE: 10
auggcuugaa gauguacucg aucuc                                              25

<210> SEQ ID NO 11
<211> LENGTH: 25
<212> TYPE: RNA
<213> ORGANISM: Artificial Sequence
<220> FEATURE:
<223> OTHER INFORMATION: synthetic construct

<400> SEQUENCE: 11
gcacacagga uggcuugaag augua                                              25

<210> SEQ ID NO 12
<211> LENGTH: 25
<212> TYPE: RNA
<213> ORGANISM: Artificial Sequence
<220> FEATURE:
<223> OTHER INFORMATION: synthetic construct

<400> SEQUENCE: 12
caggcccucg ucauugcagc agccc                                              25

<210> SEQ ID NO 13
<211> LENGTH: 25
<212> TYPE: RNA
<213> ORGANISM: Artificial Sequence
<220> FEATURE:
<223> OTHER INFORMATION: synthetic construct

<400> SEQUENCE: 13
uguuggacuc cucagugggc acaca                                              25

<210> SEQ ID NO 14
<211> LENGTH: 25
<212> TYPE: RNA
<213> ORGANISM: Artificial Sequence
<220> FEATURE:
<223> OTHER INFORMATION: synthetic construct

<400> SEQUENCE: 14
gcauggugau guuggacucc ucagu                                              25

<210> SEQ ID NO 15
<211> LENGTH: 25
<212> TYPE: RNA
<213> ORGANISM: Artificial Sequence
<220> FEATURE:
<223> OTHER INFORMATION: synthetic construct

<400> SEQUENCE: 15
uggccuuggu gagguuugau ccgca                                              25
```

```
<210> SEQ ID NO 16
<211> LENGTH: 25
<212> TYPE: RNA
<213> ORGANISM: Artificial Sequence
<220> FEATURE:
<223> OTHER INFORMATION: synthetic construct

<400> SEQUENCE: 16
ggaagcucau cucuccuaug ugcug                                           25

<210> SEQ ID NO 17
<211> LENGTH: 25
<212> TYPE: RNA
<213> ORGANISM: Artificial Sequence
<220> FEATURE:
<223> OTHER INFORMATION: synthetic construct

<400> SEQUENCE: 17
uucacauuug uugugcugua ggaag                                           25

<210> SEQ ID NO 18
<211> LENGTH: 25
<212> TYPE: RNA
<213> ORGANISM: Artificial Sequence
<220> FEATURE:
<223> OTHER INFORMATION: synthetic construct

<400> SEQUENCE: 18
uugcucuauc uuucuuuggu cugca                                           25

<210> SEQ ID NO 19
<211> LENGTH: 25
<212> TYPE: RNA
<213> ORGANISM: Artificial Sequence
<220> FEATURE:
<223> OTHER INFORMATION: synthetic construct

<400> SEQUENCE: 19
uucuugucuu gcucuaucuu ucuuu                                           25

<210> SEQ ID NO 20
<211> LENGTH: 25
<212> TYPE: RNA
<213> ORGANISM: Artificial Sequence
<220> FEATURE:
<223> OTHER INFORMATION: synthetic construct

<400> SEQUENCE: 20
acaaacaaau gcuuucuccg cucug                                           25

<210> SEQ ID NO 21
<211> LENGTH: 25
<212> TYPE: RNA
<213> ORGANISM: Artificial Sequence
<220> FEATURE:
<223> OTHER INFORMATION: synthetic construct

<400> SEQUENCE: 21
ggaacauuua cacgucugcg gaucu                                           25

<210> SEQ ID NO 22
<211> LENGTH: 25
<212> TYPE: RNA
<213> ORGANISM: Artificial Sequence
<220> FEATURE:
<223> OTHER INFORMATION: synthetic construct
```

```
<400> SEQUENCE: 22
aacucaagcu gccucgccuu gcaac                                              25

<210> SEQ ID NO 23
<211> LENGTH: 20
<212> TYPE: DNA
<213> ORGANISM: Artificial Sequence
<220> FEATURE:
<223> OTHER INFORMATION: synthetic construct

<400> SEQUENCE: 23
ctgctgtctt gggtgcattg                                                    20

<210> SEQ ID NO 24
<211> LENGTH: 20
<212> TYPE: DNA
<213> ORGANISM: Artificial Sequence
<220> FEATURE:
<223> OTHER INFORMATION: synthetic construct

<400> SEQUENCE: 24
cttccgggct cggtgattta                                                    20

<210> SEQ ID NO 25
<211> LENGTH: 25
<212> TYPE: RNA
<213> ORGANISM: Artificial Sequence
<220> FEATURE:
<223> OTHER INFORMATION: synthetic construct

<400> SEQUENCE: 25
gccugggacc acugaggaca gaaag                                              25

<210> SEQ ID NO 26
<211> LENGTH: 25
<212> TYPE: RNA
<213> ORGANISM: Artificial Sequence
<220> FEATURE:
<223> OTHER INFORMATION: synthetic construct

<400> SEQUENCE: 26
uccuucugcc augggugcag ccugg                                              25

<210> SEQ ID NO 27
<211> LENGTH: 25
<212> TYPE: RNA
<213> ORGANISM: Artificial Sequence
<220> FEATURE:
<223> OTHER INFORMATION: synthetic construct

<400> SEQUENCE: 27
gaugauucug cccuccuccu ucugc                                              25

<210> SEQ ID NO 28
<211> LENGTH: 25
<212> TYPE: RNA
<213> ORGANISM: Artificial Sequence
<220> FEATURE:
<223> OTHER INFORMATION: synthetic construct

<400> SEQUENCE: 28
acagccaggg ggacucaccu ucgug                                              25

<210> SEQ ID NO 29
```

```
<211> LENGTH: 25
<212> TYPE: DNA
<213> ORGANISM: Artificial Sequence
<220> FEATURE:
<223> OTHER INFORMATION: synthetic construct

<400> SEQUENCE: 29
acagccaggg ggactcacct tcgtg                                              25
```

METHODS FOR TREATING VEGF-RELATED CONDITIONS

CROSS-REFERENCE TO RELATED APPLICATIONS

This is a National Stage Entry under 37 U.S.C. 371 of International Patent Application No. PCT/AU2019/050438, filed May 10, 2019, which claims priority to Australian Patent Application No. 2018901653, filed May 14, 2018. These applications are incorporated by reference herein.

INCORPORATION-BY-REFERENCE OF MATERIAL SUBMITTED IN ELECTRONIC FORM

Applicant hereby incorporates by reference the Sequence Listing provided in the file named "PCTAU2019050438_ST24.txt" (created Sep. 15, 2021, 5,875 bytes).

TECHNICAL FIELD

The present invention relates to antisense oligonucleotides (AON) to induce alternative splicing through exon skipping in the vascular endothelial growth factor A (VEGF-A) gene. The invention further provides methods to treat, prevent or ameliorate the effects of a disease associated with expression of the VEGF-A gene by administration of AON and therapeutic compositions comprising AONs to the VEGF-A gene.

BACKGROUND ART

Vascular endothelial growth factor A (VEGF-A) is a key regulator of angiogenesis, a process that drives the formation of new blood vessels towards the tumour and play a vital role in cancer progression and metastasis. Previous studies have shown the overexpression of VEGF-A in numerous types of cancers such as glioblastoma, medulloblastoma, hepatocellular carcinoma, adeno carcinoma and breast cancer.

It is now evident that the functions of VEGF-A are not restricted to angiogenesis. Recent studies reported that VEGF contribute to a range of different processes, including: the regulation of immune cells in tumour microenvironment; promoting cancer cell stemness and accelerating the recurrence of cancer; and enhancing the survival of cancer stem cells along with formation of aggressive and highly vascularized tumours. Overexpression of VEGF "attracts" $CD4^+$ forkhead box protein P3 $(FOXP3)^+$ regulatory T cells, which are known to suppress anti-tumour immune response to the tumour. Sequestering VEGF increases the activation of $CD8^+$ T cell which lead to the reduction in tumour growth. Recently, Liu et al. demonstrated that increasing of plasma VEGF after radiofrequency ablation therapy advocates tumour stemness and tumourigenesis of hepatocellular carcinoma.[15] Study also suggested that VEGF upregulates cMyc and Sox2, two transcription factors involved in self-renewal ability of stem cells, indicates an important role of VEGF in driving the cancer stem cell population development.

Anti-VEGF therapy for solid cancers has been studied extensively in the past decades, with investigators trying to block either VEGF expression or the interaction between VEGF and its receptors. Another approach is to manipulate the balance between pro-angiogenic VEGF and anti-angiogenic VEGF-b isoforms, although this hypothesis is under debate since more evidence is required to confirm the existence of these VEGF-b isoforms. To date, the US Food and Drug Administration (FDA) has approved two antibody-based drugs targeting VEGF-A (Bevacizumab® and Aflibercept®), but the efficacy and side effects of these drugs leave a question mark over their future.

There is a need to provide alternative therapies targeting the VEGF-A gene; or at least the provision of therapies to compliment the previously known therapies and drugs.

The present invention seeks to provide an improved or alternative method for targeting the VEGF-A gene.

The previous discussion of the background art is intended to facilitate an understanding of the present invention only. The discussion is not an acknowledgement or admission that any of the material referred to is or was part of the common general knowledge as at the priority date of the application.

SUMMARY OF INVENTION

The present invention is directed to compounds, particularly AONs, which are targeted to a nucleic acid encoding vascular endothelial growth factor A (VEGF-A). Embodiments of the present invention relate to AONs that are capable of binding to VEGF-A pre-mRNA.

Broadly, according to one aspect of the invention, there is provided an isolated or purified AON targeted to a nucleic acid molecule encoding VEGF-A pre-mRNA, wherein the AON has a nucleobase sequence selected from the list comprising SEQ ID NO: 1 to SEQ ID NO: 22 and wherein the AON inhibits the expression of human VEGF-A. Preferably, the AON induces alternate splicing of VEGF-A pre-mRNA through exon skipping. More preferably, the AON is a phosphorodiamidate morpholino oligomer. More preferably, the AON is SEQ ID NO: 4.

The invention extends, according to a still further aspect thereof, to cDNA or cloned copies of the AON sequences of the invention, as well as to vectors containing one or more of the AON sequences of the invention. The invention extends further to cells containing such sequences and/or vectors.

There is also provided a method for inducing alternative splicing of VEGF-A pre-mRNA, the method comprising the step of: providing one or more of the AON's as described herein and allowing the oligonucleotide to bind to a target nucleic acid site.

There is also provided a pharmaceutical, prophylactic, or therapeutic composition to treat, prevent or ameliorate the effects of a disease associated with mutations in VEGF-A, the composition comprising one or more AONs as described herein; and one or more pharmaceutically acceptable carriers and/or diluents. Preferably, the disease associated with mutations in VEGF-A is solid tumour cancers, aged-related macular degeneration (AMD), diabetic retinopathy (DR), diabetic macular edema (DME) and rheumatoid arthritis (RA).

There is also provided a method for treating, preventing or ameliorating the effects of a disease associated with mutations in VEGF-A, the method comprising the step of: administering to the subject an effective amount of one or more AONs or pharmaceutical composition comprising one or more AONs as described herein.

There is also provided the use of purified and isolated AONs as described herein, for the manufacture of a medicament to treat, prevent or ameliorate the effects of a disease associated with mutations in VEGF-A.

There is also provided herein the use of purified and isolated AON as described herein, to treat, prevent or ameliorate the effects of a disease associated with mutations in VEGF-A.

There is also provided herein a kit to treat, prevent or ameliorate the effects of a disease associated with mutations in VEGF-A in a subject, which kit comprises at least an AON as described herein, packaged in a suitable container, together with instructions for its use.

Further aspects of the invention will now be described with reference to the accompanying non-limiting Examples and Drawings.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 6 is a sequencing data analysis of the skipped products.

FIG. 7A. 3 days-time point; FIG. 7B. 5 days-time point.

FIG. 8A. Western gel image visualized by chemiluminescence; FIG. 8B. Densitometry analysis of the western gel image demonstrating down-regulated percentage of VEGF-A protein in treated samples at 5 days post transfection of Vexsa2(SEQ ID NO: 4)-PMO.

DESCRIPTION OF INVENTION

Detailed Description of the Invention

Figure 1:
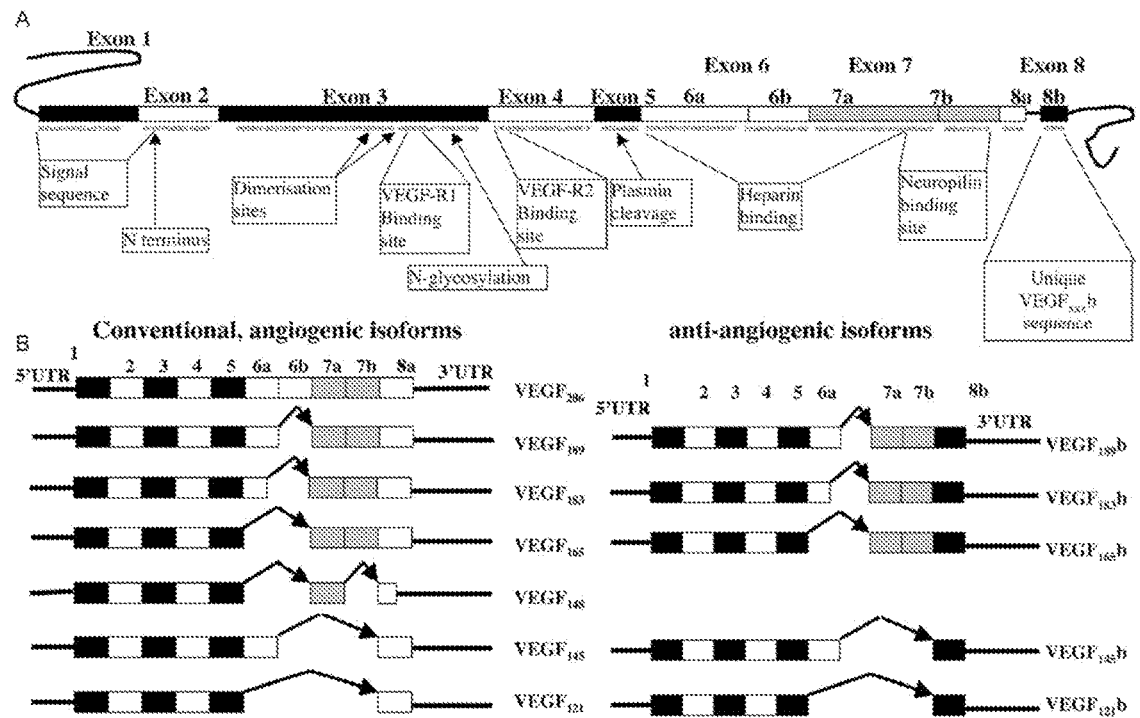
FIG. 1 is a diagram of the VEGF-A gene. The gene comprises of 8 exons and "spliced" to produce different isoforms including the three dominant forms VEGFA-165, VEGFA-121 and VEGFA-189, which overexpressed in different types of VEGF-related diseases. (Adapted from Nowak et al. 23).
Figure 2:
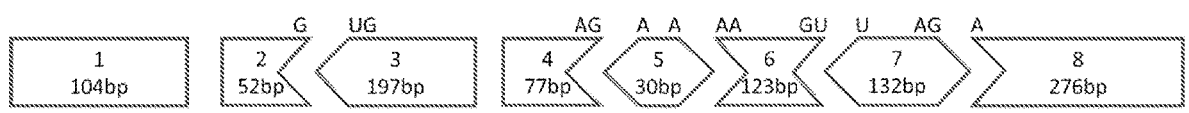
FIG. 2 is a diagram of the exons of the VEGF-A gene.

The present invention provides a prophylactic or therapeutic method for ameliorating the symptoms of disease using AON therapy. More specifically, the invention provides isolated or purified antisense oligonucleotides (AONs) that target to a nucleic acid molecule encoding vascular endothelial growth factor A (VEGF-A) pre-mRNA, wherein the AON has a nucleobase sequence selected from the list comprising SEQ ID NO: 1 to SEQ ID NO: 22 and wherein the AON inhibits the expression of VEGF-A. Preferably, the AON induces alternate splicing of VEGF-A pre-mRNA through exon skipping. More preferably, the AON is a phosphorodiamidate morpholino oligomer. More preferably, the AON is SEQ ID NO: 4.

Embodiments of the present invention relate generally to improved antisense compounds, and methods or use thereof, which are specifically designed to supress the expression of the VEGF-A gene. Expression of the VEGF-A gene has been implicated in diseases such as solid tumour cancers (glioblastoma, medulloblastoma, hepatocellular carcinoma, adeno carcinoma and breast cancer), aged-related macular degeneration (AMD), diabetic retinopathy (DR), diabetic macular edema (DME) and rheumatoid arthritis (RA).

Without being bound by theory, the present invention is based on the understanding that suppressing the expression of VEGF-A in subjects suffering from various conditions may have the effect of improving survival of these subjects. Various polymorphisms have been identified in the VEGF-A gene, and these have been associated with predisposition to cancer development and progression, and increased microvessel density. The pathogenesis has been implicated with neovascularization, a process of forming new blood vessels from the pre-existing ones. Recent studies reported that VEGF-A contributes to different processes including inflammation and cellular immunity that occurred in pathological neovascularization, including pathological retinal neovascularization. Therefore, suppression of the VEGF-A gene is hypothesised to result in improved survival of subjects and/or an increase in time to vision impairment.

The functions of VEGF-A are not restricted to angiogenesis. Recent studies reported that VEGF contributes to different processes including: regulation of immune cells in the tumour microenvironment; promoting cancer cell stemness and accelerating the recurrence of cancer; enhancing the survival of cancer stem cells; enhancing the formation of aggressive and highly vascularized tumours. VEGF also acts as pro-inflammatory cytokine targeting monocytes, macrophages and leukocytes in the neovascularization process. Sequestering VEGF increases the activation of CD8+ T-cells, which leads to a reduction in tumour growth.

Solid tumour cancers include sarcomas, carcinomas, and lymphomas. For example, solid cell cancers include glioblastoma, medulloblastoma, mesothelioma, hepatocellular carcinoma, adeno-carcinoma and breast cancer.

As VEGF-A plays a crucial role in both retinal and choroidal angiogenesis, inhibition of VEGF-A can be a suitable approach for both AMD and DR treatment. The same also applies to DME, where enhanced VEGF-A expression leads to blood retinal barrier (BRB) damage via promotion of vascular permeability and inflammation.

Preferably, the present invention provides AONs that are capable of binding a selected target on a nucleic acid molecule encoding VEGF-A so as to induce exon skipping, and consequently result in alternative splicing of the gene, no longer encoding a complete VEGF-A protein. The alternatively spliced gene will therefore result in the downregulation of the expression of the full VEGF-A protein.

Antisense Oligonucleotides

This invention provides one or more isolated or purified AONs that targets a nucleic acid molecule encoding vascular endothelial growth factor A (VEGF-A) pre-mRNA, wherein the AON has a nucleobase sequence selected from the list comprising SEQ ID NO: 1 to SEQ ID NO: 22 (Table 1, below) and wherein the AON inhibits the expression of VEGF-A. Preferably, the AON induces alternate splicing of VEGF-A pre-mRNA through exon skipping. More preferably, the AON is a phosphorodiamidate morpholino oligomer. More preferably, the AON is SEQ ID NO: 4.

In one example, targeting of exon 2 of VEGF-A induces a stop codon in exon 3, and terminates the translation of the VEGFA-165, VEGFA-121 and VEGFA-189 isoforms simultaneously.

The AONs of the invention are designed to complement suitable sequences within the human VEGF-A pre-mRNA which are required for correct splicing of the targeted exon, thereby blocking splicing reactions that would incorporate the targeted exon into mature mRNA.

The terms "antisense oligomer" and "antisense compound" and "antisense oligonucleotide" or "AON" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits are based on ribose or another pentose sugar or, in a preferred embodiment, a morpholino group (see description of morpholino oligomers below). The oligomer may have exact or near sequence complementarity to the target sequence: variations in sequence near the termini of an oligomer are generally preferable to variations in the interior.

By "isolated" it is meant material that is substantially or essentially free from components that normally accompany

TABLE 1

AONs targeting VEGF-A

| EXON | NAME | SEQUENCE | SEQ ID NO |
|---|---|---|---|
| 2 (52 bp) | VEGFA-2A(-14+11) | GCCUGGGACCAcugaggacagaaag | 1 |
|  | VEGFA-2A(+6+30) | UCCUUCUGCCAUGGGUGCAGCCUGG | 2 |
|  | VEGFA-2A(+22+46) | GAUGAUUCUGCCCUCCUCCUUCUGC | 3 |
|  | VEGFA-2D(+7-18) [Vexsa2] | acagccaggggacucacCUUCGUG | 4 |
| 3 (197 bp) | VEGFA-3A(-14+11) | GAACUUCACCAcugcaugagaggcg | 5 |
|  | VEGFA-3A(+8+32) | GCUGCGCUGAUAGACAUCCAUGAAC | 6 |
|  | VEGFA-3A(+26+50) | CUCGAUUGGAUGGCAGUAGCUGCGC | 7 |
|  | VEGFA-3A(+40+64) | AUGUCCACCAGGGUCUCGAUUGGAU | 8 |
|  | VEGFA-3A(+57+81) | CAGGGUACUCCUGGAAGAUGUCCAC | 9 |
|  | VEGFA-3A(+84+108) | AUGGCUUGAAGAUGUACUCGAUCUC | 10 |
|  | VEGFA-3A(+93+117) | GCACACAGGAUGGCUUGAAGAUGUA | 11 |
|  | VEGFA-3A(+134+158) | CAGGCCCUCGUCAUUGCAGCAGCCC | 12 |
|  | VEGFA-3A(+162+186) | UGUUGGACUCCUCAGUGGGCACACA | 13 |
|  | VEGFA-3A(+171+195) | GCAUGGUGAUGUUGGACUCCUCAGU | 14 |
| 4 (77 bp) | VEGFA-4A(+5+29) | UGGCCUUGGUGAGGUUUGAUCCGCA | 15 |
|  | VEGFA-4A(+28+52) | GGAAGCUCAUCUCUCCUAUGUGCUG | 16 |
|  | VEGFA-4A(+48+72) | UUCACAUUUGUUGUGCUGUAGGAAG | 17 |
| 5 (30 bp) | VEGFA-5A(-5+20) | UUGCUCUAUCUUUCUUUGGUcugca | 18 |
|  | VEGFA-5A(+4+28) | UUCUUGUCUUGCUCUAUCUUUCUUU | 19 |
| 6 (7) | VEGFA-7A(+18+42) | ACAAACAAAUGCUUUCUCCGCUCUG | 20 |
| (132 bp) | VEGFA-7A(+46+70) | GGAACAUUUACACGUCUGCGGAUCU | 21 |
|  | VEGFA-7A(+97+121) | AACUCAAGCUGCCUCGCCUUGCAAC | 22 |

Reverse complement sequence shown 5-3'. The reference point (0) set at first base of polyadenylation signal; hence "+" refers to sequences downstream of A$^0$ATAAA and "-" indicates sequences upstream The AONs of the present invention target the pre-mRNA (1 copy per gene) of VEGF-A. they can be used to inhibit all predominant VEGF-A isoforms expressed in various solid cancers at the gene transcript level. The AONs of the present invention can be synthesised as phosphorodiamidate morpholinos (PMOs) which have been proven to be non-toxic at high doses without any side effects in a subject. Furthermore, the AONs of the present invention can be conjugated with various chemistries (including PEG) to improve their pharmacodynamics.

it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

An AON can be said to be "directed to" or "targeted against" a target sequence with which it hybridizes. In certain embodiments, the target sequence includes a region including the polyadenylation site and surrounding regions. The target sequence is typically a region including an AUG start codon of an mRNA, a Translation Suppressing Oligomer, or splice site of a pre-processed mRNA, a Splice Suppressing Oligomer (SSO). The target sequence for a splice site may include an rRNA sequence having its 5' end 1 to about 25 base pairs downstream of a normal splice acceptor junction in a pre-processed mRNA. A preferred target sequence is any region of a pre-processed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

As used herein, "sufficient length" refers to an AON that is complementary to at least 8, more typically 8-30, contiguous nucleobases in a target VEGF-A pre-mRNA. In some embodiments, an antisense of sufficient length includes at least 8, 9, 10, 11, 12, 13, 14, or 15 contiguous nucleobases in the target VEGF-A pre-mRNA. In other embodiments an antisense of sufficient length includes at least 16, 17, 18, 19, 20, 21, 22, 23, 24, or 25 contiguous nucleobases in the target VEGF-A pre-mRNA. Preferably, an oligonucleotide of sufficient length is from about 10 to about 50 nucleotides in length, including oligonucleotides of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 or more nucleotides. In one embodiment, an oligonucleotide of sufficient length is from 10 to about 30 nucleotides in length. In another embodiment, an oligonucleotide of sufficient length is from 15 to about 25 nucleotides in length. In yet another embodiment, an oligonucleotide of sufficient length is from 20 to 30, or 20 to 50, nucleotides in length. In yet another embodiment, an oligonucleotide of sufficient length is from 22 to 28, 25 to 28, 24 to 29 or 25 to 30 nucleotides in length.

In certain embodiments, the AON has sufficient sequence complementarity to a target RNA to block a region of a target RNA (e.g., pre-mRNA) in an effective manner. In exemplary embodiments, such blocking of VEGF-A pre-RNA serves to induce exon skipping. In some embodiments, the target RNA is target pre-RNA (e.g., VEGF-A gene pre-RNA).

In certain embodiments, AONs may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability. Although such an AON is not necessarily 100% complementary to the target sequence, it is effective to stably and specifically bind to the target sequence, such that cleavage factor binding to the target pre-RNA is modulated.

The stability of the duplex formed between an AON and a target sequence is a function of the binding Tm and the susceptibility of the duplex to cellular enzymatic cleavage. The Tm of an oligonucleotide with respect to complementary-sequence RNA may be measured by conventional methods, such as those described by Hames et al., *Nucleic Acid Hybridization*, IRL Press, (1985), 107-108 or as described in Miyada C. G. and Wallace R. B., (1987), *Methods Enzymol.* 154, 94-107. In certain embodiments, AONs may have a binding Tm, with respect to a complementary-sequence RNA, of greater than body temperature and preferably greater than about 45° C. or 50° C. Tm's in the range 60-80° C. or greater are also included.

Additional examples of variants include AONs having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of SEQ ID NOS: 1-22.

More specifically, there is provided an AON capable of binding to a selected target site to induce exon skipping in a VEGF-A gene transcript or part thereof. The AON is preferably selected from those provided in Table 1. Preferably the AON is not SEQ ID NO: 8, 10, 11, 17 or 19. More preferably, the AON is SEQ ID NO: 4.

Methods of Use

The invention further provides a method of inducing alternative splicing of VEGF-A pre-mRNA, the method comprising the steps of:
  (a) providing one or more of the AONs as described herein and
  (b) allowing the oligomer(s) to bind to a target nucleic acid site.

More specifically, the AON may be selected from those set forth in Table 1. The sequences are preferably selected from the group consisting of any one or more of any one or more of SEQ ID NOs: 1-22, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate RNA processing activity in a VEGF-A gene transcript. More preferably, the AON is SEQ ID NO: 4.

The oligomer and the DNA, cDNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or pairing such that stable and specific binding occurs between the oligomer and the DNA, cDNA or RNA target. It is understood in the art that the sequence of an AON need not be 100% complementary to that of its target sequence to be specifically hybridisable. An AON is specifically hybridisable when binding of the compound to the target DNA or RNA molecule interferes with the normal function of the target DNA or RNA product, and there is a sufficient degree of complementarity to avoid non-specific binding of the AON to non-target sequences under conditions in which specific binding is desired, i.e., under physiological conditions in the case of in vivo assays or therapeutic treatment, and in the case of in vitro assays, under conditions in which the assays are performed.

Selective hybridisation may be under low, moderate or high stringency conditions, but is preferably under high stringency. Those skilled in the art will recognise that the stringency of hybridisation will be affected by such conditions as salt concentration, temperature, or organic solvents, in addition to the base composition, length of the complementary strands and the number of nucleotide base mismatches between the hybridising nucleic acids. Stringent temperature conditions will generally include temperatures in excess of 30° C., typically in excess of 37° C., and preferably in excess of 45° C., preferably at least 50° C., and typically 60° C.-80° C. or higher. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0). Thus, the AONs of the present invention may include oligomers that selectively hybridise to the sequences provided in Table 1.

At a given ionic strength and pH, the Tm is the temperature at which 50% of a target sequence hybridizes to a complementary polynucleotide. Such hybridization may occur with "near" or "substantial" complementarity of the AON to the target sequence, as well as with exact complementarity.

Typically, selective hybridisation will occur when there is at least about 55% identity over a stretch of at least about 14 nucleotides, preferably at least about 65%, more preferably at least about 75% and most preferably at least about 90%, 95%, 98% or 99% identity with the nucleotides of the antisense oligomer. The length of homology comparison, as described, may be over longer stretches and in certain embodiments will often be over a stretch of at least about nine nucleotides, usually at least about 12 nucleotides, more usually at least about 20, often at least about 21, 22, 23 or 24 nucleotides, at least about 25, 26, 27 or 28 nucleotides, at least about 29, 30, 31 or 32 nucleotides, at least about 36 or more nucleotides.

Thus, the AON sequences of the invention preferably have at least 75%, more preferably at least 85%, more preferably at least 86, 87, 88, 89 or 90% homology to the sequences shown in the sequence listings herein. More preferably there is at least 91, 92, 93 94, or 95%, more preferably at least 96, 97, 98% or 99%, homology. Generally, the shorter the length of the antisense oligomer, the greater the homology required to obtain selective hybridisation. Consequently, where an AON of the invention consists of less than about 30 nucleotides, it is preferred that the percentage identity is greater than 75%, preferably greater than 85, 86, 87, 88, 89, 90, 91, 92, 93, 94, 95%, 96, 97, 98% or 99% compared with the AONs set out in the sequence listings herein. Nucleotide homology comparisons may be conducted by sequence comparison programs such as the GCG Wisconsin Bestfit program or GAP (Deveraux et al., 1984, *Nucleic Acids Research* 12, 387-395). In this way sequences of a similar or substantially different length to those cited herein could be compared by insertion of gaps into the alignment, such gaps being determined, for example, by the comparison algorithm used by GAP.

The AON of the present invention may have regions of reduced homology, and regions of exact homology with the target sequence. It is not necessary for an oligomer to have exact homology for its entire length. For example, the oligomer may have continuous stretches of at least 4 or 5 bases that are identical to the target sequence, preferably continuous stretches of at least 6 or 7 bases that are identical to the target sequence, more preferably continuous stretches of at least 8 or 9 bases that are identical to the target sequence. The oligomer may have stretches of at least 10, 11, 12, 13, 14, 15, 16, 17, 18, 19, 20, 21, 22, 23, 24, 25 or 26 bases that are identical to the target sequence. The remaining stretches of oligomer sequence may be intermittently identical with the target sequence; for example, the remaining sequence may have an identical base, followed by a non-identical base, followed by an identical base. Alternatively (or as well) the oligomer sequence may have several stretches of identical sequence (for example 3, 4, 5 or 6 bases) interspersed with stretches of less than perfect homology. Such sequence mismatches will preferably have no or very little loss of cleavage modifying activity.

The term "modulate" or "modulates" includes to "increase" or "decrease" one or more quantifiable parameters, optionally by a defined and/or statistically significant amount. The terms "increase" or "increasing," "enhance" or "enhancing," or "stimulate" or "stimulating" refer generally to the ability of one or AONs or compositions to produce or cause a greater physiological response (i.e., downstream effects) in a cell or a subject relative to the response caused by either no AON or a control compound.

By "enhance" or "enhancing," or "increase" or "increasing," or "stimulate" or "stimulating," refers generally to the ability of one or antisense compounds or compositions to produce or cause a greater physiological response (i.e., downstream effects) in a cell or a subject, as compared to the response caused by either no antisense compound or a control compound. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc) the amount produced by no antisense compound (the absence of an agent) or a control compound.

The terms "decreasing" or "decrease" refer generally to the ability of one or AONs or compositions to produce or cause a reduced physiological response (i.e., downstream effects) in a cell or a subject relative to the response caused by either no AON or a control compound. The term "reduce" or "inhibit" may relate generally to the ability of one or more antisense compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art and may include reductions in the symptoms or pathology of a VEGF-A related condition. A "decrease" in a response may be statistically significant as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

Relevant physiological or cellular responses (in vivo or in vitro) will be apparent to persons skilled in the art and may include decreases in the amount of VEGF-A expression. An "increased" or "enhanced" amount is typically a statistically significant amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1, e.g., 1.5, 1.6, 1.7. 1.8) the amount produced by no AON (the absence of an agent) or a control compound. The term "reduce" or "inhibit" may relate generally to the ability of one or more AONs or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art and may include reductions in the symptoms or pathology of a disease associated with expression of VEGF-A, such as solid tumour cancers, aged-related macular degeneration (AMD), diabetic retinopathy (DR) and diabetic macular edema (DME). A "decrease" in a response may be statistically significant as compared to the response produced by no AON or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The length of an AON may vary, as long as it is capable of binding selectively to the intended location within the pre-RNA molecule. The length of such sequences can be determined in accordance with selection procedures described herein. Generally, the AON will be from about 10 nucleotides in length, up to about 50 nucleotides in length. It will be appreciated, however, that any length of nucleotides within this range may be used in the method. Preferably, the length of the AON is between 10 and 40, 10 and 35, 15 to 30 nucleotides in length or 20 to 30 nucleotides in length, most preferably about 25 to 30 nucleotides in length. For example, the oligomer may be 20, 21, 22, 23, 24, 25, 26, 27, 28, 29 or 30 nucleotides in length.

As used herein, an "AON" or "antisense oligonucleotide" refers to a linear sequence of nucleotides, or nucleotide analogs, that allows the nucleobase to hybridize to a target sequence in an RNA by Watson-Crick base pairing, to form an oligonucleotide:RNA heteroduplex within the target sequence. The terms "AON" or "antisense oligonucleotide", "oligomer" and "antisense compound" may be used interchangeably to refer to an oligonucleotide. The cyclic subunits may be based on ribose or another pentose sugar or, in certain embodiments, a morpholino group (see description of morpholino oligonucleotides below). Also contemplated are peptide nucleic acids (PNAs), locked nucleic acids (LNAs), and 2'-O-Methyl oligonucleotides, among other antisense agents known in the art.

In some embodiments, the AONs have the chemical composition of a naturally occurring nucleic acid molecule, i.e., the AONs do not include a modified or substituted base, sugar, or inter-subunit linkage.

In a preferred embodiment, the AONs of the present invention are non-naturally occurring nucleic acid molecules, or "oligonucleotide analogs". For example, non-naturally occurring nucleic acids can include one or more non-natural base, sugar, and/or inter-subunit linkage, e.g., a base, sugar, and/or linkage that has been modified or substituted with respect to that found in a naturally occurring nucleic acid molecule. Exemplary modifications are described below. In some embodiments, non-naturally occurring nucleic acids include more than one type of modification, e.g. sugar and base modifications, sugar and linkage modifications, base and linkage modifications, or base, sugar, and linkage modifications. For example, in some embodiments, the AONs contain a non-natural (e.g. modified or substituted) base. In some embodiments, the AONs contain a non-natural (e.g. modified or substituted) sugar. In some embodiments, the AONs contain a non-natural (e.g. modified or substituted) inter-subunit linkage. In some embodiments, the AONs contain more than one type of modification or substitution, e.g. a non-natural base and/or a non-natural sugar, and/or a non-natural inter-subunit linkage.

Thus, included are non-naturally-occurring AONs having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

One method for producing AONs is the methylation of the 2' hydroxyribose position and the incorporation of a phosphorothioate backbone produces molecules that superficially resemble RNA but that are much more resistant to nuclease degradation, although persons skilled in the art of the invention will be aware of other forms of suitable backbones that may be useable in the objectives of the invention.

To avoid degradation of pre-RNA during duplex formation with the antisense oligomers, the AONs used in the method may be adapted to minimise or prevent cleavage by endogenous RNase H. Antisense molecules that do not activate RNase H can be made in accordance with known techniques (see, e.g., U.S. Pat. No. 5,149,797). Such antisense molecules, which may be deoxyribonucleotide or ribonucleotide sequences, simply contain any structural modification which sterically hinders or prevents binding of RNase H to a duplex molecule containing the oligonucleotide as one member thereof, which structural modification does not substantially hinder or disrupt duplex formation. Because the portions of the oligonucleotide involved in duplex formation are substantially different from those portions involved in RNase H binding thereto, numerous antisense molecules that do not activate RNase H are available. This property is highly preferred, as the treatment of the RNA with the unmethylated oligomers, either intracellular or in crude extracts that contain RNase H, leads to degradation of the pre-mRNA:AON duplexes. Any form of modified AONs that is capable of by-passing or not inducing such degradation may be used in the present method. The nuclease resistance may be achieved by modifying the AONs of the invention so that it comprises partially unsaturated aliphatic hydrocarbon chain and one or more polar or charged groups including carboxylic acid groups, ester groups, and alcohol groups.

An example of an AON which when duplexed with RNA is not cleaved by cellular RNase H is an 2'-O-methyl derivative. Such 2'-O-methyl-oligoribonucleotides are stable in a cellular environment and in animal tissues, and their duplexes with RNA have higher Tm values than their ribo- or deoxyribo-counterparts. Alternatively, the nuclease resistant AONs of the invention may have at least one of the last 3'-terminus nucleotides fluoridated. Still alternatively, the nuclease resistant AONs of the invention have phosphorothioate bonds linking between at least two of the last 3-terminus nucleotide bases, preferably having phosphorothioate bonds linking between the last four 3'-terminal nucleotide bases.

Decreased RNA cleavage may also be achieved with alternative oligonucleotide chemistry (see, e.g., U.S. Pat. No. 5,149,797). For example, the AON may be chosen from the list comprising: phosphoramidate or phosphorodiamidate morpholino oligomer (PMO); PMO-X; PPMO; peptide nucleic acid (PNA); a locked nucleic acid (LNA) and derivatives including alpha-L-LNA, 2'-amino LNA, 4'-methyl LNA and 4'-O-methyl LNA; ethylene bridged nucleic acids (ENA) and their derivatives; phosphorothioate oligomer; tricyclo-DNA oligomer (tcDNA); tricyclophosphorothioate oligomer; 2'-O-Methyl-modified oligomer (2'-OMe); 2'-O-methoxy ethyl (2'-MOE); 2'-fluoro, 2'-fluoroarabino (FANA); unlocked nucleic acid (UNA); hexitol nucleic acid (HNA); cyclohexenyl nucleic acid (CeNA); 2'-amino (2'-NH2); 2'-O-ethyleneamine or any combination of the foregoing as mixmers or as gapmers.

To further improve the delivery efficacy, the abovementioned modified nucleotides are often conjugated with fatty acids/lipid/cholesterol/amino acids/carbohydrates/polysaccharides/nanoparticles etc. to the sugar or nucleobase moieties. These conjugated nucleotide derivatives can also be used to construct AONs to induce exon skipping. Antisense oligomer-induced exon skipping of the VEGF-A gene transcripts can use oligoribonucleotides, PNAs, 2OMe or MOE modified bases on a phosphorothioate backbone. Although 2OMeAONs are used for oligo design, due to their efficient uptake in vitro when delivered as cationic lipoplexes, these compounds are susceptible to nuclease degradation and are not considered ideal for in vivo or clinical applications. When alternative chemistries are used to generate the AONs of the present invention, the uracil (U) of the sequences provided herein may be replaced by a thymine (T).

For example, such antisense molecules may be oligonucleotides wherein at least one, or all, of the inter-nucleotide bridging phosphate residues are modified phosphates, such as methyl phosphonates, methyl phosphorothioates, phosphoromorpholidates, phosphoropiperazidates and phosphor amidates. For example, every other one of the inter-nucleotide bridging phosphate residues may be modified as described. In another non-limiting example, such antisense molecules are molecules wherein at least one, or all, of the nucleotides contain a 2' lower alkyl moiety (e.g., Ci-C4, linear or branched, saturated or unsaturated alkyl, such as methyl, ethyl, ethenyl, propyl, 1-propenyl, 2-propenyl, and isopropyl). For example, every other one of the nucleotides may be modified as described.

Specific examples of AONs useful in this invention include oligonucleotides containing modified backbones or non-natural intersubunit linkages.

Oligonucleotides having modified backbones include those that retain a phosphorus atom in the backbone and those that do not have a phosphorus atom in the backbone. Modified oligonucleotides that do not have a phosphorus atom in their inter-nucleoside backbone can also be considered to be oligonucleosides.

In other antisense molecules, both the sugar and the inter-nucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleo-bases are retained and are bound directly or indirectly to aza nitrogen atoms of the amide portion of the backbone.

Modified oligonucleotides may also contain one or more substituted sugar moieties. Oligonucleotides may also include nucleobase (often referred to in the art simply as "base") modifications or substitutions. Oligonucleotides containing a modified or substituted base include oligonucleotides in which one or more purine or pyrimidine bases most commonly found in nucleic acids are replaced with less common or non-natural bases.

Purine bases comprise a pyrimidine ring fused to an imidazole ring; adenine and guanine are the two purine nucleobases most commonly found in nucleic acids. These may be substituted with other naturally-occurring purines, including but not limited to $N_6$-methyladenine, $N_2$-methylguanine, hypoxanthine, and 7-methylguanine.

Pyrimidine bases comprise a six-membered pyrimidine ring; cytosine, uracil, and thymine are the pyrimidine bases most commonly found in nucleic acids. These may be substituted with other naturally-occurring pyrimidines, including but not limited to 5-methylcytosine, 5-hydroxymethylcytosine, pseudouracil, and 4-thiouracil. In one embodiment, the oligonucleotides described herein contain thymine bases in place of uracil.

Other modified or substituted bases include, but are not limited to, 2,6-diaminopurine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and $N_4$-ethylcytosine, or derivatives thereof; $N_2$-cyclopentylguanine (cPent-G), $N_2$-cyclopentyl-2-aminopurine (cPent-AP), and $N_2$-propyl-2-aminopurine (Pr-AP), pseudouracil or derivatives thereof; and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G and Super T can be found in U.S. Pat. No. 6,683,173 (Epoch Biosciences). cPent-G, cPent-AP and Pr-AP were shown to reduce immunostimulatory effects when incorporated in siRNA (Peacock H. et al. *J. Am. Chem. Soc.* 2011, 133, 9200). Pseudouracil is a naturally occurring isomerized version of uracil, with a C-glycoside rather than the regular N-glycoside as in uridine. Pseudouridine-containing synthetic mRNA may have an improved safety profile compared to uridine-containing mPvNA (see WO 2009127230).

Certain modified or substituted nucleo-bases are particularly useful for increasing the binding affinity of the AONs of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

In some embodiments, modified or substituted nucleobases are useful for facilitating purification of AONs. For example, in certain embodiments, AONs may contain three or more (e.g., 3, 4, 5, 6 or more) consecutive guanine bases. In certain AONs, a string of three or more consecutive guanine bases can result in aggregation of the oligonucleotides, complicating purification. In such AONs, one or more of the consecutive guanines can be substituted with inosine. The substitution of inosine for one or more guanines in a string of three or more consecutive guanine bases can reduce aggregation of the AON, thereby facilitating purification.

In one embodiment, another modification of the AONs involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a given compound to be uniformly modified, and in fact more than one of the aforementioned modifications may be incorporated in a single compound or even at a single nucleoside within an oligonucleotide. The present invention also includes AONs that are chimeric compounds. "Chimeric" antisense compounds or "chimeras," in the context of this invention, are antisense molecules, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the increased resistance to nuclease degradation, increased cellular uptake, and an additional region for increased binding affinity for the target nucleic acid.

The antisense molecules used in accordance with this invention may be conveniently and routinely made through the well-known technique of solid phase synthesis. Equipment for such synthesis is sold by several vendors including, for example, Applied Biosystems (Foster City, Calif.). One method for synthesising oligonucleotides on a modified solid support is described in U.S. Pat. No. 4,458,066.

In another non-limiting example, such AONs are molecules wherein at least one, or all, of the nucleotides contain a 2' lower alkyl moiety (such as, for example, C1-C4, linear or branched, saturated or unsaturated alkyl, such as methyl, ethyl, ethenyl, propyl, 1-propenyl, 2-propenyl, and isopropyl). For example, every other one of the nucleotides may be modified as described.

While the AONs described above are a preferred form of the AONs of the present invention, the present invention includes other oligomeric antisense molecules, including but not limited to oligomer mimetics such as are described below.

Another preferred chemistry is the phosphorodiamidate morpholino oligomer (PMO) oligomeric compounds, which are not degraded by any known nuclease or protease. These compounds are uncharged, do not activate RNase H activity when bound to a RNA strand and have been shown to exert sustained cleavage factor binding modulation after in vivo administration (Summerton and Weller, *Antisense Nucleic Acid Drug Development*, 7, 187-197).

Modified oligomers may also contain one or more substituted sugar moieties. Oligomers may also include nucleobase (often referred to in the art simply as "base") modifications or substitutions. Certain nucleobases are particularly useful for increasing the binding affinity of the oligomeric compounds of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C., even more particularly when combined with 2'-O-methoxyethyl sugar modifications. In one embodiment, at least one pyrimidine base of the oligonucleotide comprises a 5-substituted pyrimidine base, wherein the pyrimidine base is selected from the group consisting of cytosine, thymine and uracil. In one embodiment, the 5-substituted pyrimidine base is 5-methylcytosine. In another embodiment, at least one purine base of the oligonucleotide comprises an N-2, N-6 substituted purine base. In one embodiment, the N-2, N-6 substituted purine base is 2, 6-diaminopurine.

In one embodiment, the AON includes one or more 5-methylcytosine substitutions alone or in combination with another modification, such as 2'-O-methoxyethyl sugar modifications. In yet another embodiment, the AON includes one or more 2, 6-diaminopurine substitutions alone or in combination with another modification.

In some embodiments, the AON is chemically linked to one or more moieties, such as a polyethylene glycol moiety, or conjugates, such as an arginine-rich cell penetrating peptide that enhance the activity, cellular distribution, or cellular uptake of the AON. In one exemplary embodiment, the arginine-rich polypeptide is covalently coupled at its N-terminal or C-terminal residue to the 3' or 5' end of the antisense compound. Also, in an exemplary embodiment, the antisense compound is composed of morpholino subunits and phosphorus-containing inter-subunit linkages joining a morpholino nitrogen of one subunit to a 5' exocyclic carbon of an adjacent subunit.

In another aspect, the invention provides expression vectors that incorporate the AONs described above, e.g., the AONs of SEG ID NOs: 1-22. In some embodiments, the expression vector is a modified retrovirus or non-retroviral vector, such as an adeno-associated viral vector.

Another modification of the oligomers of the invention involves chemically linking to the oligomer one or more moieties or conjugates that enhance the activity, cellular distribution or cellular uptake of the oligomer. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, myristyl, or an octadecylamine or hexylamino-carbonyl-oxycholesterol moiety.

Cell penetrating peptides have been added to phosphorodiamidate morpholino oligomers to enhance cellular uptake and nuclear localization. Different peptide tags have been shown to influence efficiency of uptake and target tissue specificity, as shown in Jearawiriyapaisarn et al. (2008), *Mol. Ther.*, 16(9), 1624-1629. The terms "cell penetrating peptide" and "CPP" are used interchangeably and refer to cationic cell penetrating peptides, also called transport peptides, carrier peptides, or peptide transduction domains. The peptides, as shown herein, have the capability of inducing cell penetration within 100% of cells of a given cell culture population and avow macromolecular translocation within multiple tissues in vivo upon systemic administration.

It is not necessary for all positions in a given compound to be uniformly modified, and in fact more than one of the aforementioned modifications may be incorporated in a single compound or even at a single nucleoside within an oligomer. The present invention also includes AONs that are chimeric compounds. "Chimeric" AONs or "chimeras," in the context of this invention, are antisense oligomers, particularly oligomers, which contain two or more chemically distinct regions, each made up of at least one monomer unit, i.e., a nucleotide in the case of an oligomer compound. These oligomers typically contain at least one region wherein the oligomer is modified so as to confer upon the oligomer or AON increased resistance to nuclease degradation, increased cellular uptake, and an additional region for increased binding affinity for the target nucleic acid.

The activity of AONs and variants thereof can be assayed according to routine techniques in the art. For example, isoform forms and expression levels of surveyed RNAs and proteins may be assessed by any of a wide variety of well-known methods for detecting isoforms and/or expression of a transcribed nucleic acid or protein. Non-limiting examples of such methods include RT-PCR of isoforms of RNA followed by size separation of PCR products, nucleic acid hybridization methods e.g., Northern blots and/or use of nucleic acid arrays; fluorescent in situ hybridization to detect RNA transcripts inside cells; nucleic acid amplification methods; immunological methods for detection of proteins; protein purification methods; and protein function or activity assays.

RNA expression levels can be assessed by preparing RNA/cDNA (i.e., a transcribed polynucleotide) from a cell, tissue or organism, and by hybridizing the RNA/cDNA with a reference polynucleotide, which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcripT1(s).

The AONs used in accordance with this invention may be conveniently made through the well-known technique of solid phase synthesis. Equipment for such synthesis is sold by several vendors including, for example, Applied Biosystems (Foster City, Calif.). One method for synthesising oligomers on a modified solid support is described in U.S. Pat. No. 4,458,066.

Any other means for such synthesis known in the art may additionally or alternatively be employed. It is well known to use similar techniques to prepare oligomers such as the phosphorothioates and alkylated derivatives. In one such automated embodiment, diethyl-phosphoramidites are used as starting materials and may be synthesized as described by Beaucage, et al., (1981) *Tetrahedron Letters,* 22:1859-1862.

The AONs of the invention are synthesised in vitro and do not include antisense compositions of biological origin, or genetic vector constructs designed to direct the in vivo synthesis of antisense oligomers. The molecules of the invention may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

Also included are vector delivery systems that are capable of expressing the oligomeric, VEGF-A-targeting sequences of the present invention, such as vectors that express a polynucleotide sequence comprising any one or more of SEQ ID NOs: 1-22, as described herein. Preferably the AON is not SEQ ID NO: 8, 10, 11, 17 or 19. More preferably, the AON is SEQ ID NO: 4.

By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof or be integrable with the genome of the defined host such that the cloned sequence is reproducible.

Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

Method of Treatment

The AONs of the present invention also can be used as a prophylactic or therapeutic, which may be utilised for the purpose of treatment of a disease. Accordingly, in one embodiment the present invention provides AONs that bind to a selected target in the VEGF-A RNA to modify cleavage of the RNA as described herein, in a therapeutically effective amount, admixed with a pharmaceutically acceptable carrier, diluent, or excipient.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

Preferably the subject is an animal, preferably a mammal, most preferably a human.

The invention therefore provides a pharmaceutical, prophylactic, or therapeutic composition to treat, prevent or ameliorate the effects of a disease associated with expression of VEGF-A, the composition comprising:

a) one or more AONs as described herein, and
b) one or more pharmaceutically acceptable carriers and/or diluents.

Preferably, the disease associated with expression of VEGF-A is solid tumour cancers, aged-related macular degeneration (AMD), diabetic retinopathy (DR) and diabetic macular edema (DME).

Preferably, the AON used in the present invention is chosen from the list of AONs provided in Table 1 or more preferably is SEQ ID NO: 4.

The composition may comprise about 1 nM to 1000 nM of each of the desired antisense oligomer(s) of the invention. Preferably, the composition may comprise about 1 nM to 500 nM, 10 nM to 500 nM, 50 nM to 750 nM, 10 nM to 500 nM, 1 nM to 100 nM, 1 nM to 50 nM, 1 nM to 40 nM, 1 nM to 30 nM, 1 nM to 20 nM, most preferably between 1 nM and 10 nM of each of the antisense oligomer(s) of the invention.

The composition may comprise about 1 nm, 2 nm, 3 nm, 4 nm, 5 nm, 6 nm, 7 nm, 8 nm, 9 nm, 10 nm, 20 nm, 50 nm, 75 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm of each of the desired antisense oligomer(s) of the invention.

The present invention further provides one or more AONs adapted to aid in the prophylactic or therapeutic treatment, prevention or amelioration of symptoms of a disease or pathology associated with mutations to VEGF-A in a form suitable for delivery to a subject.

The phrase "pharmaceutically acceptable" refers to molecular entities and compositions that are physiologically tolerable and do not typically produce an allergic or similarly untoward reaction, such as gastric upset and the like, when administered to a subject. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, Remington's Pharmaceutical Sciences, 18th Ed., Mack Publishing Co., Easton, PA, (1990).

Pharmaceutical Compositions

In a form of the invention there are provided pharmaceutical compositions comprising therapeutically effective amounts of one or more AONs of the invention together with pharmaceutically acceptable diluents, preservatives, solubilizers, emulsifiers, adjuvants, and/or carriers. Such compositions include diluents of various buffer content (e.g. Tris-HCl, acetate, phosphate), pH and ionic strength and additives such as detergents and solubilizing agents (e.g. Tween 80, Polysorbate 80), anti-oxidants (e.g., ascorbic acid, sodium metabisulfite), preservatives (e.g. Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, for example, Martin, *Remington's Pharmaceutical Sciences*, 18th Ed. (1990, Mack Publishing Co., Easton, PA 18042) pages 1435-1712 that are herein incorporated by reference. The compositions may be prepared in liquid form, or may be in dried powder, such as a lyophilised form.

It will be appreciated that pharmaceutical compositions provided according to the present invention may be administered by any means known in the art. Preferably, the pharmaceutical compositions for administration are administered by injection, orally, topically or by the pulmonary or nasal route. The AONs are more preferably delivered by intravenous, intra-arterial, intraperitoneal, intramuscular or subcutaneous routes of administration. The appropriate route may be determined by one of skill in the art, as appropriate to the condition of the subject under treatment. Vascular or extravascular circulation, the blood or lymph system, and the cerebrospinal fluid are some non-limiting sites where the AON may be introduced. Direct CNS delivery may be employed, for instance, intracerebral ventribular or intrathecal administration may be used as routes of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860 and/or U.S. patent application Ser. No. 09/315,298 filed on May 20, 1999.

In certain embodiments, the AONs of the disclosure can be delivered by transdermal methods (e.g., via incorporation of the AONs into, e.g., emulsions, with such AONs optionally packaged into liposomes). Such transdermal and emulsion/liposome-mediated methods of delivery are described for delivery of AONs in the art, e.g., in U.S. Pat. No. 6,965,025.

The AONs described herein may also be delivered via an implantable device. Design of such a device is an art-recognized process, with, e.g., synthetic implant design described in, e.g., U.S. Pat. No. 6,969,400.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860. Oral formulations for oligomers and their preparation are described in detail in U.S. Pat. Nos. 6,887,906, 09/315,298 filed May 20, 1999 and/or US20030027780.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

The delivery of a therapeutically useful amount of AONs may be achieved by methods previously published. For example, intracellular delivery of the AON may be via a composition comprising an admixture of the AON and an effective amount of a block copolymer. An example of this method is described in US patent application US20040248833. Other methods of delivery of AONs to the nucleus are described in Mann C J et al. (2001) *Proc, Natl. Acad. Science,* 98(1) 42-47, and in Gebski et al. (2003) *Human Molecular Genetics,* 12(15): 1801-1811. A method for introducing a nucleic acid molecule into a cell by way of an expression vector either as naked DNA or complexed to lipid carriers, is described in U.S. Pat. No. 6,806,084.

In certain embodiments, the AONs of the invention and therapeutic compositions comprising the same can be delivered by transdermal methods (e.g., via incorporation of the AONs into, e.g., emulsions, with such AONs optionally packaged into liposomes). Such transdermal and emulsion/liposome-mediated methods of delivery are described for delivery of AONs in the art, e.g., in U.S. Pat. No. 6,965,025.

It may be desirable to deliver the AON in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. These colloidal dispersion systems can be used in the manufacture of therapeutic pharmaceutical compositions.

Liposomes are artificial membrane vesicles, which are useful as delivery vehicles in vitro and in vivo. These formulations may have net cationic, anionic, or neutral charge characteristics and have useful characteristics for in vitro, in vivo and ex vivo delivery methods. It has been shown that large unilamellar vesicles can encapsulate a substantial percentage of an aqueous buffer containing large macromolecules. RNA and DNA can be encapsulated within the aqueous interior and be delivered to cells in a biologically active form (Fraley, et al., 1981, *Trends Biochem.* Sci., 6, 77).

In order for a liposome to be an efficient gene transfer vehicle, the following characteristics should be present: (1) encapsulation of the AON of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., 1988 *Biotechniques,* 6, 682). The composition of the liposome is usually a combination of phospholipids, particularly high phase-transition-temperature phospholipids, usually in combination with steroids, especially cholesterol. Other phospholipids or other lipids may also be used. The physical characteristics of liposomes depend on pH, ionic strength, and the presence of divalent cations. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The AONs described herein may also be delivered via an implantable device. Design of such a device is an art-recognized process, with, e.g., synthetic implant design described in, e.g., U.S. Pat. No. 6,969,400, the contents of which are incorporated in their entirety by reference herein.

AONs can be introduced into cells using art-recognized techniques (e.g., transfection, electroporation, fusion, liposomes, colloidal polymeric particles and viral and non-viral vectors as well as other means known in the art). The method of delivery selected will depend at least on the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, AONs may be delivered using, for example, methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, *Advanced Drug Delivery Reviews* 44, 35-49, incorporated by reference in its entirety).

The AON may also be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral, or transdermal administration.

The routes of administration described are intended only as a guide since a skilled practitioner will be able to readily determine the optimum route of administration and any dosage for any particular animal and condition.

Multiple approaches for introducing functional new genetic material into cells, both in vitro and in vivo have been attempted (Friedmann (1989) *Science,* 244, 1275-1280). These approaches include integration of the gene to be expressed into modified retroviruses (Friedmann (1989) supra; Rosenberg (1991) *Cancer Research* 51(18), suppl.: 5074S-5079S); integration into non-retrovirus vectors (Rosenfeld, et al. (1992) Cell, 68, 143-155; Rosenfeld, et al. (1991) *Science,* 252, 431-434); or delivery of a transgene linked to a heterologous promoter-enhancer element via liposomes (Friedmann (1989), supra; Brigham, et al. (1989) *Am. J. Med. Sci.,* 298, 278-281; Nabel, et al. (1990) *Science,* 249, 1285-1288; Hazinski, et al. (1991) *Am. J. Resp. Cell Molec. Biol.,* 4:206-209; and Wang and Huang (1987) *Proc. Natl. Acad. Sci.* (USA), 84, 7851-7855); coupled to ligand-specific, cation-based transport systems (Wu and Wu (1988) *J. Biol. Chem.,* 263, 14621-14624) or the use of naked DNA, expression vectors (Nabel et al. (1990), supra); Wolff et al. (1990) *Science,* 247, 1465-1468). Direct injection of transgenes into tissue produces only localized expression (Rosenfeld (1992) supra); Rosenfeld et al. (1991) supra; Brigham et al. (1989) supra; Nabel (1990) supra; and Hazinski et al. (1991) supra). The Brigham et al. group ((1989) *Am. J. Med. Sci.* 298, 278-281 and Clinical Research (1991) 39 (abstract)) have reported in vivo transfection only of lungs of mice following either intravenous or intratracheal administration of a DNA liposome complex. An example of a review article of human gene therapy procedures is: Anderson, (1992) *Science* 256, 808-813; Barteau et al. (2008), *Curr Gene Ther.,* 8(5), 313-23; Mueller et al. (2008). *Clin Rev*

*Allergy Immunol.*, 35(3), 164-78; Li et al. (2006) *Gene Ther.*, 13(18), 1313-9; Simoes et al. (2005) *Expert Opin Drug Deliv.*, 2(2), 237-54.

The AONs of the invention encompass any pharmaceutically acceptable salts, esters, or salts of such esters, or any other compound which, upon administration to an animal including a human, is capable of providing (directly or indirectly) the biologically active metabolite or residue thereof. Accordingly, as an example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e. salts that retain the desired biological activity of the parent compound and do not impart undesired toxicological effects thereto. For oligomers, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be topical (including ophthalmic and mucous membranes, as well as rectal delivery), pulmonary, e.g., by inhalation or insufflation of powders or aerosols (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Preferably, the AON is delivered via the subcutaneous or intravenous route.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipients(s). In general, the formulations are prepared by uniformly and intimately bringing into association the active ingredients with liquid carriers or finely divided solid carriers or both, and then, if necessary, shaping the product.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. size, concentration etc). A range of values will be understood to include all values within the range, including the values defining the range, and values adjacent to the range which lead to the same or substantially the same outcome as the values immediately adjacent to that value which defines the boundary to the range. For example, a person skilled in the field will understand that a 10% variation in upper or lower limits of a range can be totally appropriate and is encompassed by the invention. More particularly, the variation in upper or lower limits of a range will be 5% or as is commonly recognised in the art, whichever is greater.

In this application, the use of the singular also includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

Throughout this specification, unless the context requires otherwise, the word "comprise" or variations such as "comprises" or "comprising", will be understood to imply the inclusion of a stated integer or group of integers but not the exclusion of any other integer or group of integers.

As used herein, the term "administer" refers to the placement of a composition into a subject by a method or route which results in at least partial localization of the composition at its desired site of action such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

The following Examples are to be construed as merely illustrative and not limitative of the remainder of the disclosure in any way whatsoever. These Examples are included solely for the purposes of exemplifying the present invention. They should not be understood as a restriction on the broad summary, disclosure or description of the invention as set out above. Without further elaboration, it is believed that one skilled in the art can, using the preceding description, utilize the present invention to its fullest extent. In the foregoing and in the following examples, all temperatures are set forth uncorrected in degrees Celsius; and, unless otherwise indicated, all parts and percentages are by weight.

EXAMPLES

Further features of the present invention are more fully described in the following non-limiting Examples. This description is included solely for the purposes of exemplifying the present invention. It should not be understood as a restriction on the broad description of the invention as set out above.

Example 1

Design and Synthesis of Antisense Oligonucleotides

Phosphorothioated (PS) 2'-O-Methyl AOs (Table 1) were designed and prepared in-house on GE AKTA Oligopilot 10 synthesizer (GE Healthcare Life Sciences, Parramatta, NSW, Australia) via standard phosphoramidite chemistry in 1 µmol scale. The synthesized oligonucleotides were deprotected and cleaved from the solid support by treatment with $NH_4OH$ at 55° C. overnight. The crude oligonucleotides were then purified, desalted and verified by polyacrylamide gel electrophoresis. Vexsa2(SEQ ID NO: 4)-PMO was ordered from Gene Tools (Philomath, Oregon, USA).

Cell Culture and Transfection

Human cancer cell lines including DAOY (HTB-186), triple-negative breast cancer cell line MDA-MB231 (HTB-26) were obtained from American Type Culture Collection (Manassas, VA, USA); mesothelioma cell line (CBA-0143) was obtained from Cell Bank Australia (Westmead, NSW, Australia). All three cell lines were cultured in 10% Fetal Bovine Serum (FBS) Dulbecco's Modified Eagle's Medium (DMEM) (Thermo Fisher Scientific, Scoresby, VIC, Australia) in a humidified atmosphere at 37° C., 5% $CO_2$. Cells were cultured to reach 70-90% confluency, then seeded at a density of $2.5 \times 10^4$ (cells/ml) for DAOY, $1 \times 10^5$ (cells/ml) for MDA-MB231 and $5 \times 10^4$ (cells/ml) for ONE58 into 24-well plates (Thermo Fisher Scientific) 24 hours prior to transfection. The day after, the exon-skipping AOs were transfected at 400 nM concentration using Lipofectamine 3000 following the manufacturer's protocols for screening purpose. It was also noted that the best performing AO (Vexsa2-2'OMePS) was then transfected using the same protocol but at lower doses at 5, 10, 25 and 50 nM. Twenty-four hours after transfection, the cells were collected for RNA extraction.

In addition, Vexsa2(SEQ ID NO: 4)-PMO was transfected into DAOY cells at 50, 250 and 1250 nM final concentrations by nucleofection method using Primary P3 Nucleofection kit (Lonza, Waverley, VIC, Australia). Briefly, for each treatment, $6 \times 10^5$ cells were trypsinised, centrifuged and resuspended in Nucleofection master mix following manufacturer's protocol. Then, the cells were nucleofected with Vexsa2(SEQ ID NO: 4)-PMO using program CA-137 by 4D-Nucleofector system X-unit (Lonza). Cells were collected either at 3 days or 5 days timepoints for further analysis.

RNA Extraction and RT-PCR

RNA was extracted from transfected cells using Directzol™ RNA MiniPrep Plus with TRI Reagent® (Zymo Research, supplied through Integrated Sciences, Chatswood, NSW, Australia) as per the manufacturer's instructions. The VEGF-A165 and VEGF-A121 products were amplified using the primer set shown in Table 2 with SuperScript® III One-Step RT-PCR kit (Thermo Fisher Scientific). Briefly, the conditions were 55° C., 30 minutes; 94° C., 2 minutes following by 34 cycles of 94° C., 1 minute, 58° C., 30 seconds and 68° C., 1 minute. The PCR products were then separated on a 2% agarose gel in Trisz-acetate-EDTA buffer and visuallized with Fusion Fx gel documentation system (Vilber Lourmat, Marne-la-Vallee, France). Densitometry was performed by Image J software.

Sequencing

Bandstab technique was performed following the guidelines from Anthony and James. The bandstab samples were then amplified with the same primer set (Table 2) using AmpliTaq Gold® DNA Polymerase kit (Thermo Fisher Scientific). Briefly, the conditions were 94° C., 6 minutes following by 35 cycles of 94° C., 30 seconds, 52° C., 1 minute and 72° C., 2 minutes. PCR products were confirmed by 2% agarose gels and sent for sequencing using both the forward primer and reverse primer (Table 2).

Results

Exon-Skipping is Achieved at Various Levels with Different AOs Targeting Exon 2, 3, 4, 5, 6 in VEGF-A Transcript in a Triple-Negative Breast Cancer Cell Line The fully-modified 2'-O-Methyl (2'-OMe) PS AOs (Table 1) were designed to target various exons of VEGF-A transcript. The AOs were synthesized in-house by GE AKTA Oligopilot 10 on a phosphorothioate (PS) backbone via standard phosphoramidite chemistry in 1 µmol scale. The synthesized oligonucleotides were deprotected and cleaved from the solid support by treatment with $NH_4OH$ at 55° C. overnight. The crude oligonucleotides were then desalted and verified by polyacrylamide gel electrophoresis.

We have screened these AOs in a triple-negative breast cancer cell line MDA-MB231 at 400 nM concentration. Briefly, the cells were plated 24 hrs allowing to reach optimum confluency before transfection of the AO. All transfections were carried out using Lipofectamine 3000 transfection reagent following the manufacturer's protocol. Twenty-four hours after transfection, RNA was extracted using Zymo column and RT-PCR reactions were performed by Superscript III kit with the primer pair showed in Table 2 (VEGFA-Ex1F(1048-1067)/VEGFA-Ex6R (1783-1764)). The PCR products were analysed on a 3% agarose gel at 110V for 2.5 hrs.

Figure 3:
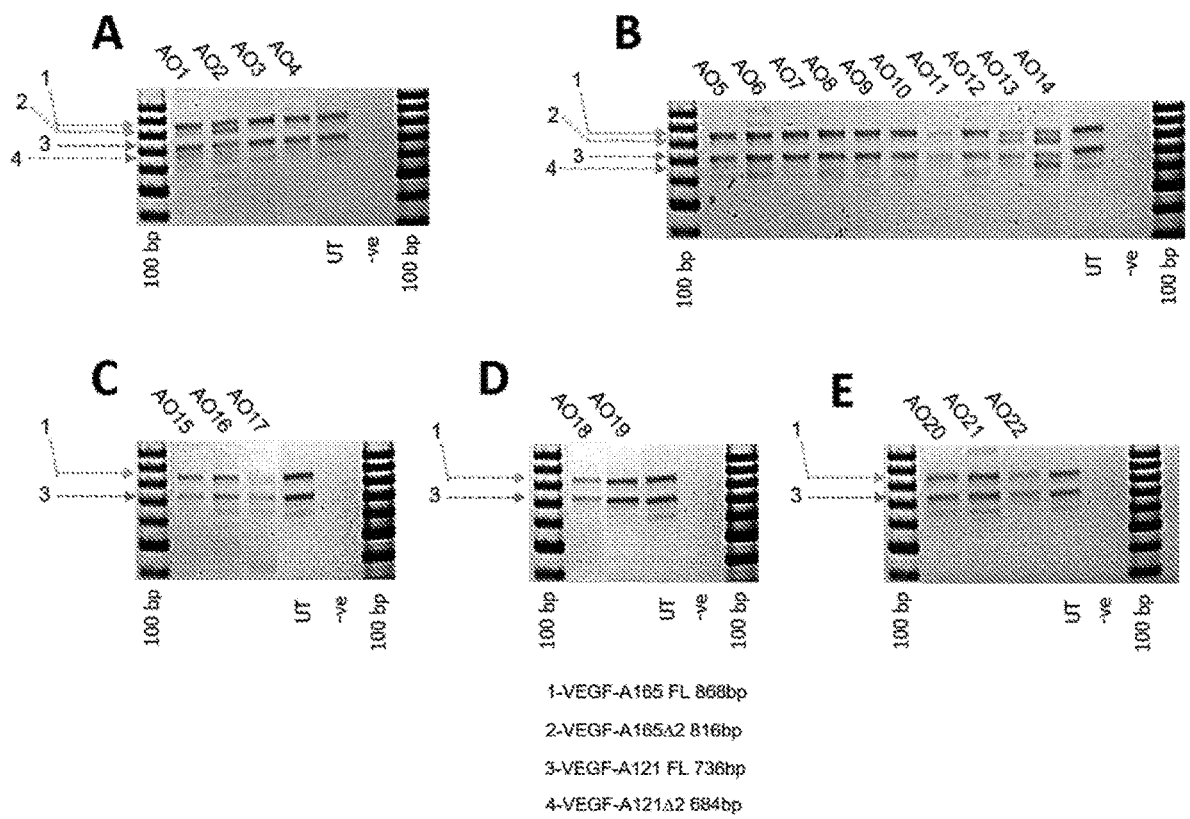
FIG. 3 is a gel electrophoresis image of RT-PCR analysis showing the screening results of various exon-skipping induced by AONs shown in Table 1 including exon-2 skipping induced by Vexsa2(SEQ ID NO: 4) in VEGF-A transcript in MDA-MB231 (triple-negative breast cancer cell line) at 400 nM.

The RT-PCR results clearly showed the VEGF-A dominant isoforms such as 165 and 121 were efficiently skipped, especially those targeting exon 2 (FIG. 3).

Exon 2 is Efficiently Skipped in VEGF-A Transcript when Treated with AO (Vexsa2(SEQ ID NO: 4)) in Various Types of Solid Cancers We then screened the AOs specifically targeting exon 2 (Table 2) in DAOY (medulloblastoma cell line). Briefly, the cells were plated 24 hrs allowing to reach optimum confluency before transfection of the AO. Then, AO1, 2, 3, 4 targeting exon 2 were transfected at 400, 600 and 800 nM concentrations to DAOY cells following abovementioned protocol.

Figure 4:
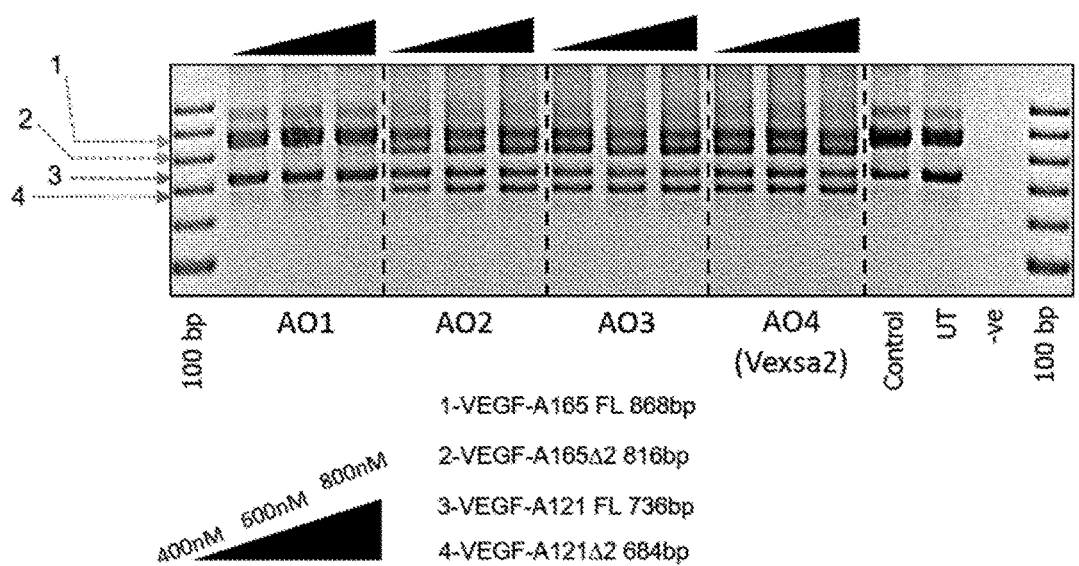
FIG. 4 is a gel electrophoresis image of RT-PCR analysis showing the results of exon-2 skipping induced by AONs specifically targeting exon 2 (Table 2) including Vexsa2 (SEQ ID NO: 4) in VEGF-A transcript in DAOY (medulloblastoma cell line) at 400, 600 and 800 nM concentrations.

The RT-PCR results clearly showed the VEGF-A dominant isoforms such as 165 and 121 exon-2 were efficiently skipped at all concentrations, and VEGFA-2D (+7-18) (AO4 or Vexsa2(SEQ ID NO: 4)) was found to be the best one in inducing exon 2-skipping (FIG. 4). The AO targets the region within the exon-2 and intron 2-3 junction.

TABLE 2

Oligonucleotide name and sequence used in this study

| NAME | CHEMISTRY | SEQUENCE (5'-3') | SEQ ID NO |
|---|---|---|---|
| VEGFA-2A(-14+11) | 2'OMePS | GCCUGGGACCAcugaggacagaaag | 25 |
| VEGFA-2A(+6+30) | 2'OMePS | UCCUUCUGCCAUGGGUGCAGCCUGG | 26 |
| VEGFA-2A(+22+46) | 2'OMePS | GAUGAUUCUGCCCUCCUCCUUCUGC | 27 |
| VEGFA-2D (+7-18) [Vexsa2] | 2'OMePS | acagccaggggacucacCUUCGUG | 28 |
| VEGFA-2D (+7-18) [Vexsa2-PMO] | PMO | acagccaggggactcacCTTCGTG | 29 |
| VEGFA-Ex1F(1048-1067) | DNA | CTGCTGTCTTGGGTGCATTG | 23 |
| VEGFA-Ex6R (1783-1764) | DNA | CTTCCGGGCTCGGTGATTTA | 24 |

Next, numerous cancer cell lines were tested with Vexsa2 (SEQ ID NO: 4) including DAOY (medulloblastoma), ONE58 (Mesothelioma), MDA-MB231 (triple-negative breast cancer) following previous protocol.

Figure 5:
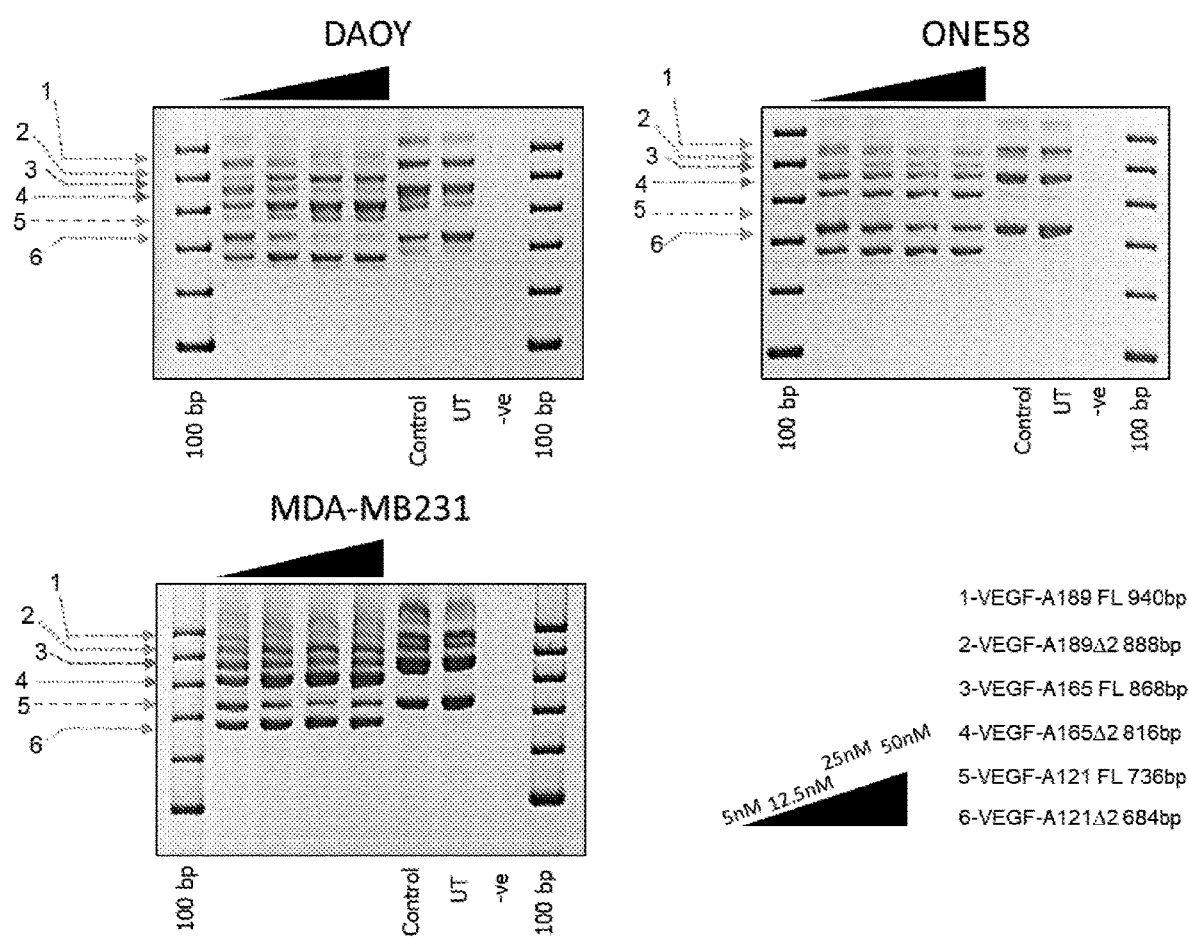
FIG. 5 is a gel electrophoresis image of RT-PCR analysis showing the results of exon-2 skipping induced by Vexsa2 (SEQ ID NO: 4) in VEGF-A transcript in DAOY (medulloblastoma cell line); ONE58 (mesothelioma cell line) and MDA-MB231 (triple-negative breast cancer cell line).

The RT-PCR results clearly showed the VEGF-A dominant isoforms such as 165, 121 and 189 exon-2 were efficiently skipped (FIG. 5 and Table 3).

TABLE 3

Percentage of exon-2 skipping in various solid cancer cell lines

| | DAOY | | | ONE58 | | | MDA-MB231 | | |
|---|---|---|---|---|---|---|---|---|---|
| | 165 | 121 | 189 | 165 | 121 | 189 | 165 | 121 | 189 |
| 5 nM | 44 | 40 | 17 | 48 | 43 | 29 | 58 | 55 | 64 |
| 10 nM | 64 | 58 | 57 | 60 | 53 | 45 | 75 | 69 | 84 |
| 25 nM | 84 | 87 | 90 | 67 | 62 | 53 | 81 | 77 | 91 |
| 50 nM | 89 | 83 | 95 | 65 | 58 | 50 | 76 | 69 | 84 |

Figure 6A:
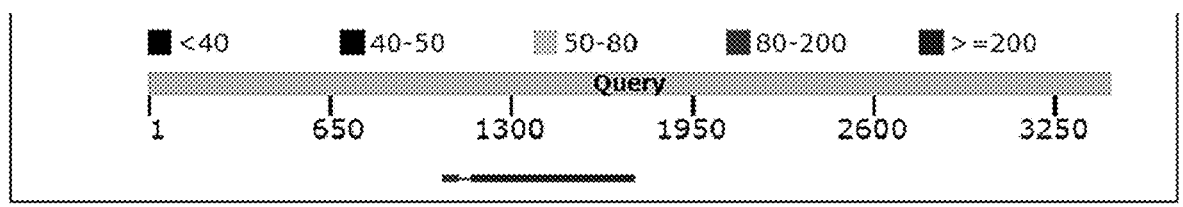
FIG. 6A. Alignment results showed efficiently skipping of exon 2 in VEGF-A 121 isoforms.
Figure 6B:
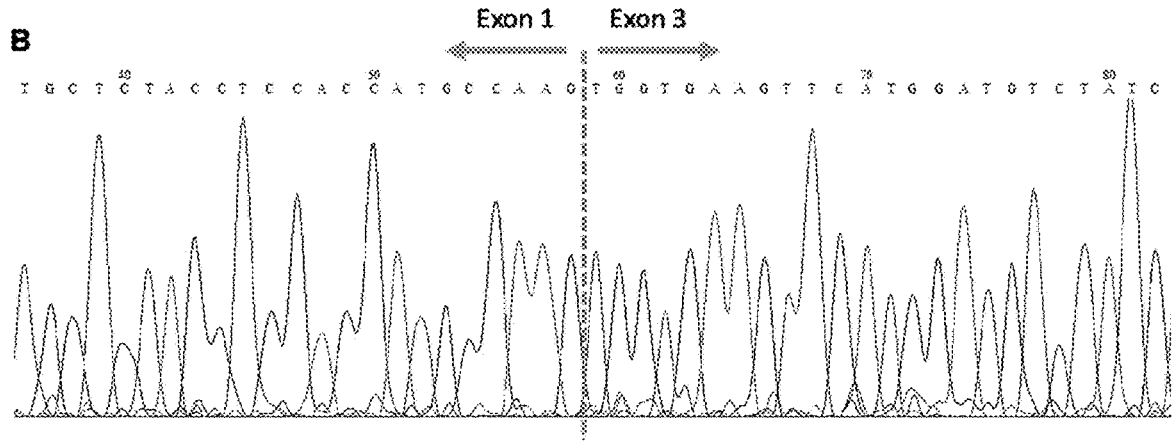
FIG. 6B. Exon 2 skipping in a base-specific manner.

The agarose gels were then band-stabbed to generate samples for sequencing. As expected, the alignment results showed skipping of exon 2 (FIG. 6A). Further analysis of sequencing results using Bioedit software demonstrated the skipping of exon 2 in a base-specific manner (FIG. 6B).

Example 2

VEGF-A is Down-Regulated at Protein Level when Treated with Exon-Skipping AO (Vexsa2(SEQ ID NO: 4)-PMO) in Medulloblastoma Cell Line Western Blot Western blotting was performed to evaluate the effect of Vexsa2(SEQ ID NO: 4)-PMO toward inhibition of VEGF protein in comparison to untreated sample. Frozen transfected cell pellets were thawed and homogenized in SDS lysis buffer (0.5 M Tris-HCl pH 6.8, 3% SDS (w/v) and 10% glycerol (v/v)) containing protease inhibitor (Sigma, Castle Hill, NSW, Australia). The homogenate was then centrifuged at 14,000 g for 3 minutes, after which the supernatant was removed, and the protein concentration of the supernatant was estimated using Pierce™ BCA Protein Assay Kit (Thermo Fisher Scientific). Protein from the samples was then resolved on a 10% SDS polyacrylamide gel under reducing conditions and electrotransferred onto a nitrocellulose membrane (Biorad, Gladesville, NSW, Australia). The membrane was processed with primary anti-VEGF antibody (1:1000) (ab46154, Abcam, Melbourne, VIC, Australia) and secondary anti-rabbit HRP antibody (1:10000) (Cat. 31460, Thermo Fisher Scientific) using iBind Flex Western Device (Thermo Fisher Scientific) following manufacturer's instructions. The protein bands were visualized with a chemiluminescence-based procedure using the Clarity Western ECL detection kit according to the manufacturers protocol (Biorad). From the positive results at mRNA level, we then ordered the AO Vexsa2(SEQ ID NO: 4) in PMO chemistry (Vexsa2-PMO) and tested in DAOY cell line. The cells were plated onto T25 flasks 24 hrs prior to nucleofection. The day after, the AO was nucleofected into cells using Lonza nucleofection system unit X at 50 nM, 250 nM and 1250 nM final concentrations. Then, the cells were harvested after 3 days and 5 days and the samples were divided for both RNA extraction and western blot.

Figure 7:
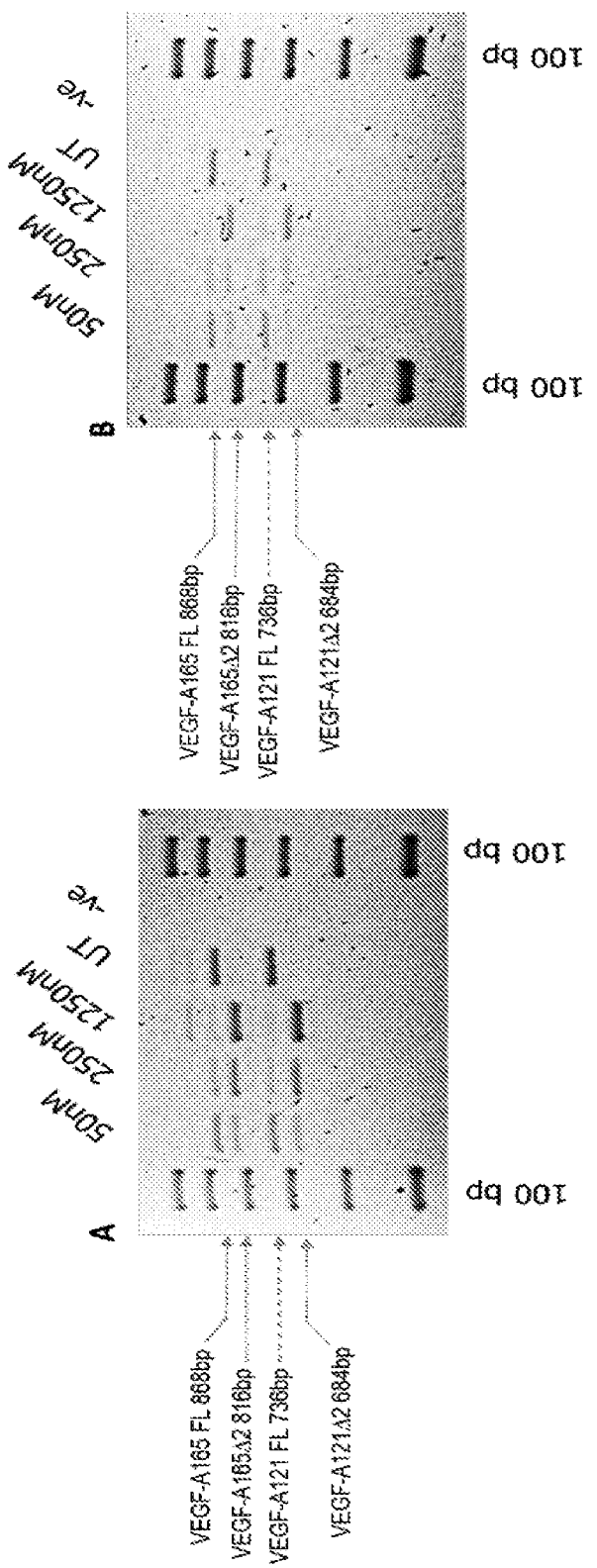
FIG. 7 is a gel electrophoresis image of RT-PCR analysis showing the results of exon-2 skipping induced by Vexsa2 (SEQ ID NO: 4)-PMO in VEGF-A transcript.

The RNA extraction and RT-PCR were performed as mentioned above. The gel results clearly showed that exon-2 was efficiently skipped in the VEGF-A transcript both at 3 days and 5 days timepoints (FIG. 7).

Figure 8:
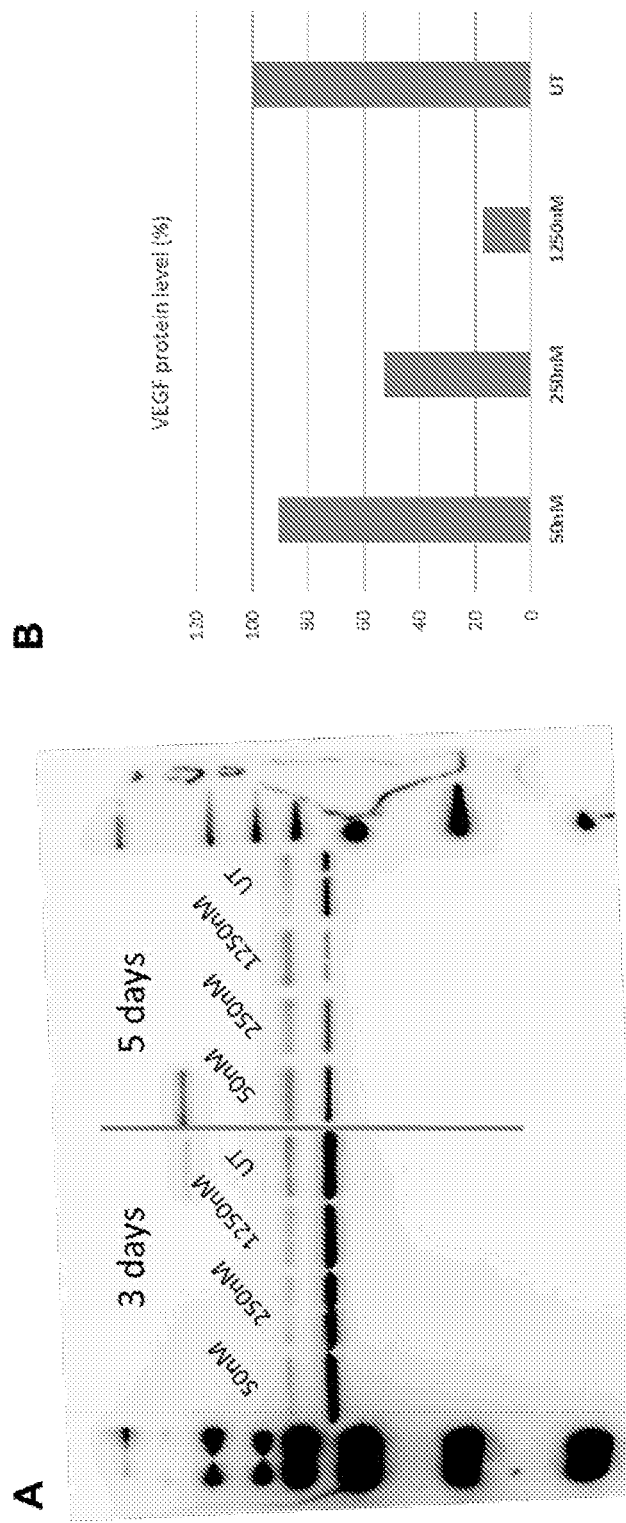
FIG. 8 is a Western blot gel image showing the results of VEGF downregulation after exon-2 skipping in DAOY cells.

A Western blot was then used to determine the protein level of VEGF-A after the AO treatment. Briefly, the protein samples were run on the SDS 10% gel and transferred to a nitrocellulose membrane. Then, the VEGF-A primary antibody (1:1000) and secondary HRP antibody (1:2000) were added to the iBind Flex Western Device for 2.5 hrs before visualized under chemiluminescent with the ECL substrate. The results indicated that the VEGF-A protein was down-regulated in the treated samples and the effect was most obvious after 5 days-time point (FIG. 8A). Densitometry analysis by Image J software revealed that at 5 days-time point, the VEGF protein was down-regulated 9%, 47% and 83% in comparison to the untreated sample (FIG. 8B).

Example 3

Exon 2 is Efficiently Skipped in VEGF-A Transcript when Treated with the AOs (Vexsa2(SEQ ID NO: 4) and Vexsa2 (SEQ ID NO: 4)-PMO) in an In Vitro Angiogenesis Model of Human Umbilical Vein Endothelial Cell (HUVEC)

HUVEC is a well-known in vitro angiogenesis model which is ideal to further evaluate the exon-skipping efficiency of the Vexsa2(SEQ ID NO: 4) AO. The cell line was obtained from Thermo Fisher Scientific and cultured in 20% FBS DMEM/F12 medium (ATCC) supplemented with low serum growth supplement (LSGS, Thermo Fisher Scientific). Once reach 70-90% confluency, cells were seeded at a density of 3×10⁴ (cells/ml) into a 24 well-plate and incubated for 24 hrs before transfected with the Vexsa2 (SEQ ID NO: 4) AO at 25, 50, 100, 200, 400 and 800 nM concentrations using Lipofectamine 3000 following the manufacturer's protocol. Twenty-four hours after transfection, the cells were collected for RNA extraction and RT-PCR was performed as abovementioned. In addition, Vexsa2 (SEQ ID NO: 4)-PMO was transfected into HUVEC cells at 500 and 2500 nM final concentrations by nucleofection method using Primary P3 Nucleofection kit (Lonza, Waverley, VIC, Australia). Briefly, for each treatment, 3×10⁵ cells were trypsinised, centrifuged and resuspended in Nucleofection master mix following manufacturer's protocol. Then, the cells were nucleofected with Vexsa2(SEQ ID NO: 4)-PMO using program CA-167 by 4D-Nucleofector system X-unit (Lonza). Cells were collected at 48 hrs timepoints for further analysis.

Figure 9:
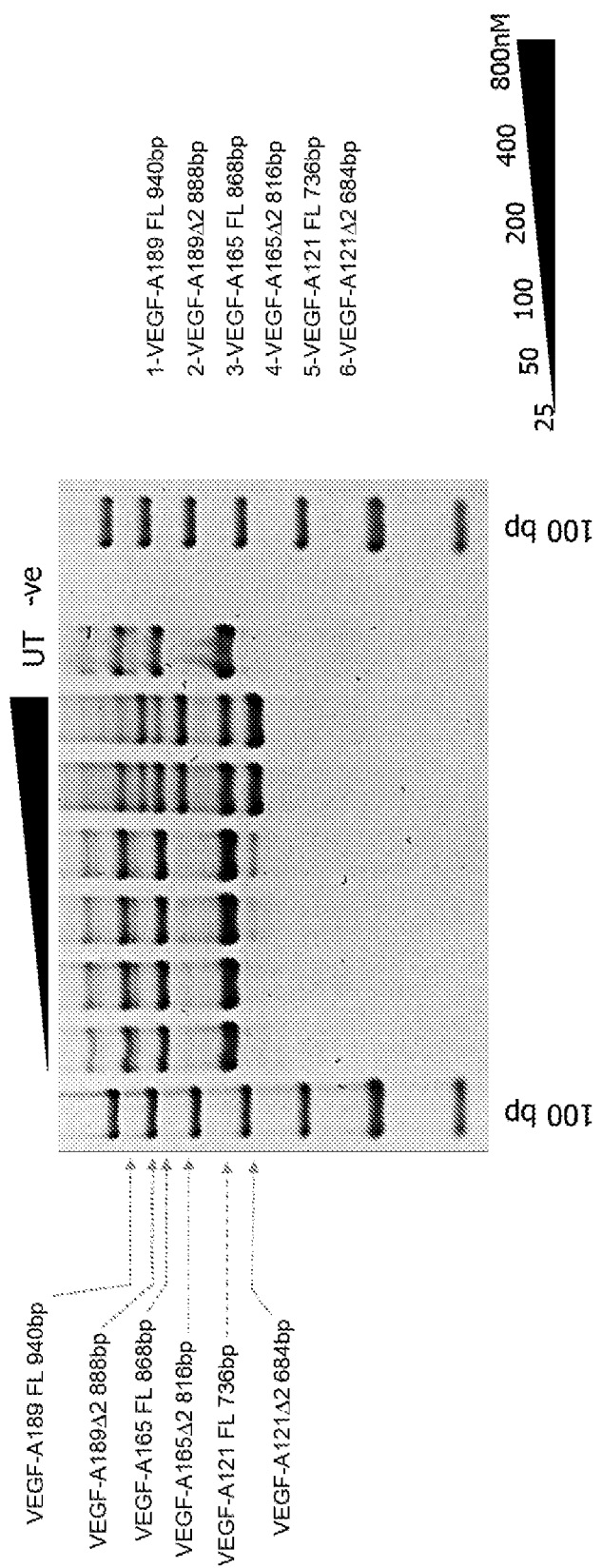
FIG. 9 is a gel electrophoresis image of RT-PCR analysis showing the results of exon-2 skipping induced by Vexsa2 (SEQ ID NO: 4) in VEGF-A transcript in angiogenesis model HUVEC cell line.
Figure 10:
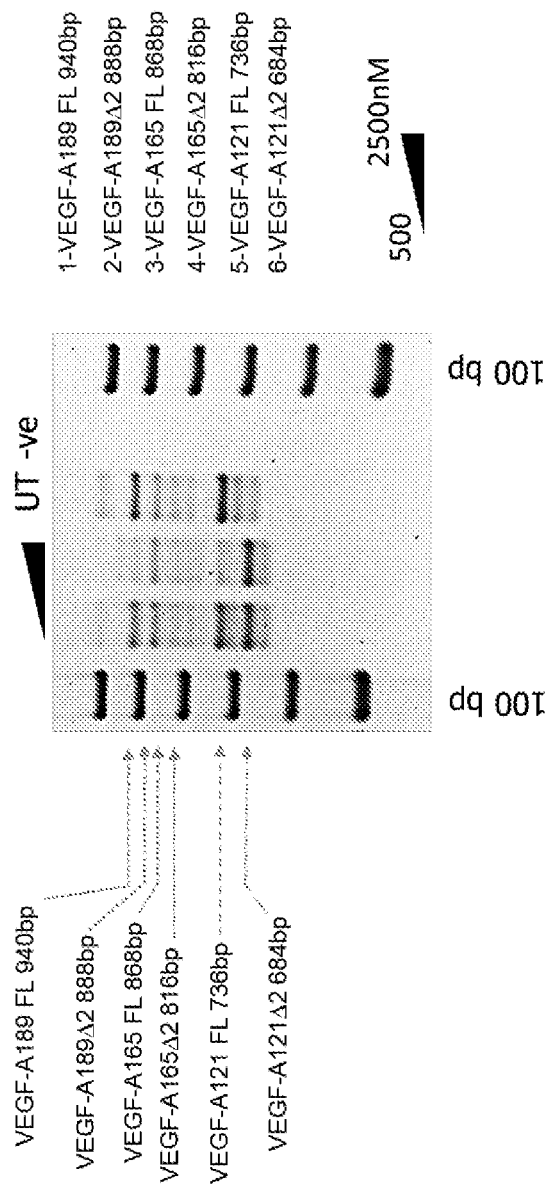
FIG. 10 is a gel electrophoresis image of RT-PCR analysis showing the results of exon-2 skipping induced by Vexsa2 (SEQ ID NO: 4)-PMO in VEGF-A transcript in angiogenesis model HUVEC cell line.

The RT-PCR results clearly showed the VEGF-A dominant isoforms such as 165, 121 and 189 exon-2 were efficiently skipped in HUVEC cell lines following a dose-dependent manner except the VEGF-A165 at 200 nM (FIG. 9 and Table 4). The gel also demonstrated that at 48 hrs timepoint after nucleofected with the Vexsa2(SEQ ID NO: 4)-PMO, VEGF-A dominant isoforms such as 189, 165 and 121 were efficiently skipped (FIG. 10).

TABLE 4

Percentage of exon-2 skipping in HUVEC cell line
HUVEC

|        | 165 | 121 | 189 |
|--------|-----|-----|-----|
| 25 nM  | 0   | 0   | 0   |
| 50 nM  | 0   | 0   | 0   |
| 100 nM | 13  | 6   | 0   |
| 200 nM | 8   | 14  | 0   |
| 400 nM | 52  | 53  | 42  |
| 800 nM | 74  | 62  | 75  |

Example 4

Exon 2 is Efficiently Skipped in VEGF-A Transcript when Treated with the AOs (Vexsa2(SEQ ID NO: 4) and Vexsa2 (SEQ ID NO: 4)-PMO) in a Human Retinal Cell Line h1RPE7

Toward the treatment of VEGF-related eye diseases such as aged-related macular degeneration (AMD), diabetic retinopathy (DR) and diabetic macular edema (DME), we further evaluated the Vexsa-2(SEQ ID NO: 4) AO efficiency in a human retinal cell line h1RPE7. Cells were obtained from Cell Bank Australia and cultured in 20% FBS Hams F10 (Thermo Fisher Scientific). Once reach 70-90% confluency, cells were seeded at a density of 4×10⁴ (cells/ml) into a 24 well plate. The AO were then transfected into h1RPE7 cells at 25, 50, 100, 200, 400 nM concentrations using Lipofectamine RNAiMax following the manufacturer's protocol. Twenty-four hours after transfection, the cells were collected for RNA extraction and RT-PCR was performed as abovementioned. In addition, Vexsa2(SEQ ID NO: 4)-PMO was transfected into h1RPE7 cells at 500 and 2500 nM final concentrations by nucleofection method using the abovementioned protocol except 6×10⁵ cells were trypsinised and the program EA-10⁴ was used. Cells were then collected at 48 hrs timepoints for further analysis.

Figure 11:
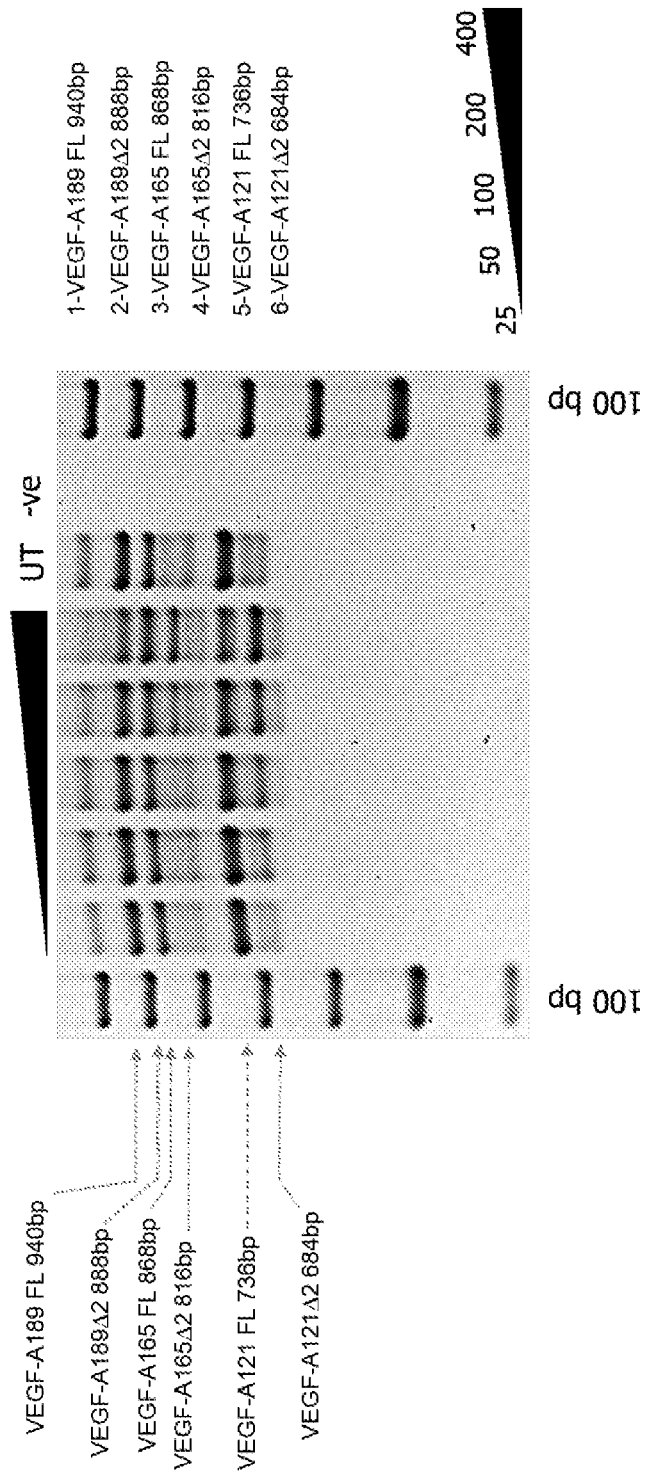
FIG. 11 is a gel electrophoresis image of RT-PCR analysis showing the results of exon-2 skipping induced by Vexsa2 (SEQ ID NO: 4) in VEGF-A transcript in human retinal cell line h1RPE7.
Figure 12:
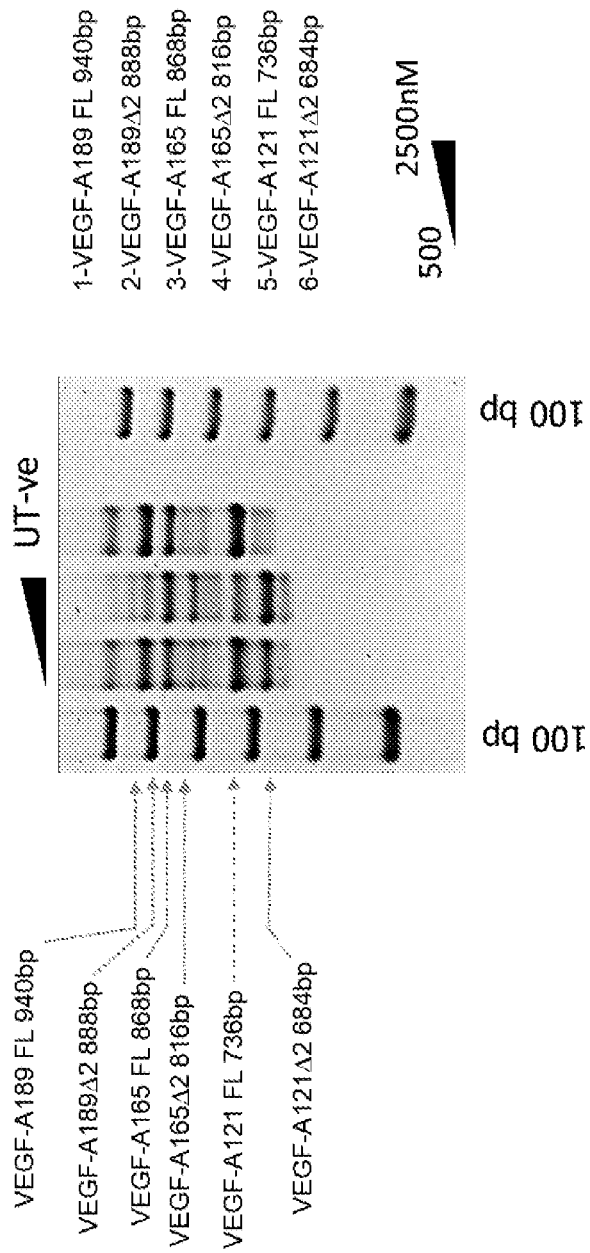
FIG. 12 is a gel electrophoresis image of RT-PCR analysis showing the results of exon-2 skipping induced by Vexsa2 (SEQ ID NO: 4)-PMO in VEGF-A transcript in human retinal cell line h1RPE7.

The RT-PCR results clearly showed the VEGF-A dominant isoforms such as 165, 121 and 189 exon-2 were efficiently skipped in h1RPE7 cell lines following a dose-dependent manner (FIG. 11 and Table 5). The gel also demonstrated that at 48 hrs timepoint after nucleofected with the Vexsa2(SEQ ID NO: 4)-PMO, VEGF-A dominant isoforms such as 189, 165 and 121 were efficiently skipped (FIG. 12).

TABLE 5

Percentage of exon-2 skipping in h1RPE7 cell line
h1RPE7

|        | 165 | 121 | 189 |
|--------|-----|-----|-----|
| 25 nM  | 15  | 11  | 0.5 |
| 50 nM  | 23  | 18  | 2   |
| 100 nM | 31  | 29  | 5   |
| 200 nM | 51  | 45  | 25  |
| 400 nM | 76  | 62  | 63  |

REFERENCES

1. Folkman, J., Merler, E., Abernathy, C., & Williams, G. (1971). ISOLATION OF A TUMOUR FACTOR RESPONSIBLE FOR ANGIOGENESIS. *J. Exp. Med.* 133, 275-288.
2. Folkman J. (1971). Tumour angiogenesis: therapeutic implications. *N. Engl. J. Med.* 285, 1182-1186.
3. Matsumoto, K., Ema, M. (2014). Roles of VEGF-A signalling in development, regeneration, and tumours. *J. Biochem.* 156, 1-10.
4. Woolard, J., Bevan, H. S., Harper, S. J., & Bates, D. O. (2009). Molecular Diversity of VEGF-A as a Regulator of Its Biological Activity. *Microcirculation* 16, 572-592.
5. Tonini, T., Rossi, F., Claudio, P. P. (2003). Molecular basis of angiogenesis and cancer. *Oncogene* 22, 6549-6556.
6. Scappaticci, F. A. (2002). Mechanisms and future directions for angiogenesis-based cancer therapies. *J. Clin. Oncol.* 20, 3906-3927.
7. Cristofanilli, M., Charnsangavej, C., Hortobagyi, G. N. (2002). Angiogenesis modulation in cancer research: novel clinical approaches. *Nat. Rev. Drug Discov.* 1, 415-426.
8. Vasudev, N. S., & Reynolds, A. R. (2014). Anti-angiogenic therapy for cancer: current progress, unresolved questions and future directions. *Angiogenesis* 17, 471-494.
9. Ferrara, N. (2004). Vascular endothelial growth factor as a target for anticancer therapy. *Oncologist* 9, 2-10.
10. Nagy, J. A., Dvorak, A. M., Dvorak, H. F. (2007). VEGF-A and the induction of pathological angiogenesis. *Annu. Rev. Pathol.* 2, 251-275.
11. Chekhonin, V. P., Shein, S. A., Korchagina, A. A., Gurina, O. I. (2013). VEGF in tumour progression and targeted therapy. *Curr. Cancer Drug Targets.* 13, 423-443.
12. Cao, Y. (2005). Tumour angiogenesis and therapy. *Biomed. Pharmacother.* 59, 340-343.
13. Sitohy, B., Nagy, J. A., & Dvorak, H. F. (2012). Anti-VEGF/VEGFR therapy for cancer: Reassessing the target. *Cancer Res.* 72, 1909-1914.
14. Goel, H. L., & Mercurio, A. M. (2013). VEGF targets the tumour cell. *Nat. Rev. Cancer* 13, 871-882.
15. Liu, K., Hao, M., Ouyang, Y., Zheng, J., & Chen, D. (2017). CD133+ cancer stem cells promoted by VEGF accelerate the recurrence of hepatocellular carcinoma. *Sci. Rep.* 7, 41499.

16. Grun, D., Adhikary, G., & Eckert, R. (2016). VEGF-A acts via neuropilin-1 to enhance epidermal cancer stem cell survival and formation of aggressive and highly vascularized tumours. *Oncogene* 35, 4379-4387.
17. Zhao, D., Pan, C., Sun, J., Gilbert, C., Drews-Elger, K., Azzam, D. J., et al. (2015). VEGF drives cancer-initiating stem cells through VEGFR-2/Stat3 signaling to upregulate Myc and Sox2. *Oncogene* 34, 3107-3119.
18. Bellou, S., Pentheroudakis, G., Murphy, C., Fotsis, T. (2013). Anti-angiogenesis in cancer therapy: Hercules and hydra. *Cancer Lett.* 338, 219-228.
19. McNamara, D. A., Harmey, J. H., Walsh, T. N., Redmond, H. P., Bouchier-Hayes, D. J. (1998). Significance of angiogenesis in cancer therapy. *Br. J. Surg.* 85, 1044-1055.
20. Young, R. J., Reed, M. W. Anti-angiogenic therapy: concept to clinic. Microcirculation 19, 115-125.
21. Harper, S. J., & Bates, D. O. (2008). VEGF-A splicing: the key to anti-angiogenic therapeutics? *Nat. Rev. Cancer.* 8, 880-887.
22. Nowak, D. G., Amin, E. M., Rennel, E. S., Hoareau-Aveilla, C., Gammons, M., Damodoran, G., et al. (2010). Regulation of Vascular Endothelial Growth Factor (VEGF) Splicing from Pro-angiogenic to Anti-angiogenic Isoforms: A NOVEL THERAPEUTIC STRATEGY FOR ANGIOGENESIS. *J. Biol. Chem.* 285, 5532-5540.
23. Nowak, D. G., Woolard, J., Amin, E. M., Konopatskaya, O., Salaam, M. A., Churchill, A. J., et al. (2008). Expression of pro- and anti-angiogenic isoforms of VEGF is differentially regulated by splicing and growth factors. *J. Cell Sci.* 121, 3487-3495.
24. Biselli-Chicote, P. M., Oliveira, A. R., Pavarino, E. C., Goloni-Bertollo, E. M. (2012). VEGF gene alternative splicing: pro- and anti-angiogenic isoforms in cancer. *J. Cancer Res. Clin. Oncol.* 138, 363-70.
25. Catena, R., Larzabal, L., Larrayoz, M., Molina, E., Hermida, J., Agorreta, J., et al. (2010). VEGF121b and VEGF165b are weakly angiogenic isoforms of VEGF-A. *Mol. Cancer* 9, 320.
26. Harris, S., Craze, M., Newton, J., Fisher, M., Shima, D. T., Tozer, G. M., & Kanthou, C. (2012). Do Anti-Angiogenic VEGF (VEGF)xxx(b) Isoforms Exist? A Cautionary Tale. *PLoS ONE* 7, e35231.
27. Keating, G. M. (2014). Bevacizumab: a review of its use in advanced cancer. *Drugs* 74, 1891-1925.
28. Ahmadizar, F., Onland-Moret, N. C., de Boer, A., Liu, G., & Maitland-van der Zee, A. H. (2015). Efficacy and Safety Assessment of the Addition of Bevacizumab to Adjuvant Therapy Agents in Cancer Subjects: A Systematic Review and Meta-Analysis of Randomized Controlled Trials. *PLoS ONE* 10, e0136324.
29. Syed, Y. Y., McKeage, K. (2015). Aflibercept: A Review in Metastatic Colorectal Cancer. *Drugs* 75, 1435-1445.
30. Jayson, G., Kerbel, R., Ellis, L. M., & Harris, A. L. (2016). Antiangiogenic therapy in oncology: current status and future directions. *The Lancet* 388, 518-529.
31. Ladomery, M. R., Harper, S. J., Bates, D. O. (2007). Alternative splicing in angiogenesis: the vascular endothelial growth factor paradigm. *Cancer Lett.* 249, 133-142.
32. Arcondeguy, T., Lacazette, E., Millevoi, S., Prats, H., & Touriol, C. (2013). VEGF-A mRNA processing, stability and translation: a paradigm for intricate regulation of gene expression at the post-transcriptional level. *Nucleic Acids Res.* 41, 7997-8010.
33. Bao, T. L., Veedu, R. N., Fletcher, S., and Wilton, S. D. (2016). Antisense oligonucleotide development for the treatment of muscular dystrophies. *Expert Opin. Orphan Drugs* 4, 139-152.
34. Bjourson, A. J., Cooper, J. E. (1992). Band-stab per: A simple technique for the purification of individual PCR products. *Nucleic Acids Res.* 20, 4675.
35. Yoo, S.-A., Kwok, S.-K., & Kim, W.-U. (2008). Proinflammatory Role of Vascular Endothelial Growth Factor in the Pathogenesis of Rheumatoid Arthritis: Prospects for Therapeutic Intervention. *Mediators Inflamm.* 2008, 129873.
36. Cantatore, F. P., Maruotti, N., Corrado, A., & Ribatti, D. (2017). Anti-angiogenic effects of biotechnological therapies in rheumatic diseases. *Biologics* 11, 123-128.
37. Leblond A., Allanore Y., Avouac J. (2017). Targeting synovial neoangiogenesis in rheumatoid arthritis. *Autoimmun Rev.* 16, 594-601.
38. Kim, H.-R., Kim, K.-W., Kim, B.-M., Cho, M.-L., & Lee, S.-H. (2015). The Effect of Vascular Endothelial Growth Factor on Osteoclastogenesis in Rheumatoid Arthritis. *PLoS ONE* 10, e0124909.

The invention claimed is:

1. An isolated or purified antisense oligonucleotide targeted to a nucleic acid molecule encoding vascular endothelial growth factor A (VEGF-A) pre-mRNA, wherein the antisense oligonucleotide has the nucleobase sequence selected from the list comprising SEQ ID NOs: 1-10, 12-14, 18 and 20-22 which have a modified backbone structure, and sequences with at least 95% sequence identity to SEQ ID NOs: 1-10, 12-14, 18 and 20-22 which have a modified backbone structure, and wherein the antisense oligonucleotide inhibits the expression of human VEGF-A.

2. The antisense oligonucleotide of claim 1 that induces alternative splicing of VEGF-A pre-mRNA through exon skipping.

3. The antisense oligonucleotide of claim 1 wherein the antisense oligonucleotide contains one or more nucleotide positions subject to an alternative chemistry or modification chosen from the list comprising: (i) modified sugar moieties; or (ii) oligomeric mimetic chemistry.

4. The antisense oligonucleotide of claim 1 wherein the antisense oligomer is further modified by: (i) chemical conjugation to a moiety; and/or (ii) tagging with a cell penetrating peptide.

5. The antisense oligonucleotide of claim 1 wherein, if a uracil is present in the antisense oligomer, the uracil (U) of the antisense oligomer is replaced by a thymine (T).

6. The antisense oligonucleotide of claim 1 that is a phosphorodiamidate morpholino oligomer.

7. The antisense oligonucleotide of claim 1 that is a 2'-O-Methyl RNA oligomer.

8. The antisense oligonucleotide of claim 1 that is SEQ ID NO: 4.

9. A method of inducing alternative splicing of VEGF-A pre-mRNA, the method comprising the steps of:
   a) providing one or more of the antisense oligonucleotides according to claim 1; and
   b) allowing the oligonucleotide(s) to bind to a target nucleic acid site.

10. A pharmaceutical, prophylactic, or therapeutic composition to treat or ameliorate the effects of a disease associated with mutations in VEGF-A, the composition comprising:
    a) one or more antisense oligonucleotides according to claim 1; and
    b) one or more pharmaceutically acceptable carriers and/or diluents.

11. The pharmaceutical composition of claim 10 wherein the disease associated with VEGF-A is a solid tumour cancer, aged-related macular degeneration, diabetic retinopathy, rheumatoid arthritis or diabetic macular edema.

12. A method of treating or ameliorating the effects of a disease associated with VEGF-A, the method comprising the step of:
    a) administering to the subject an effective amount of one or more antisense oligonucleotides or pharmaceutical composition comprising one or more antisense oligonucleotides according to claim 1.

13. The method of treatment of claim 12 wherein the disease associated with VEGF-A is a solid tumour cancer, aged-related macular degeneration, diabetic retinopathy, rheumatoid arthritis or diabetic macular edema.

14. An expression vector comprising the antisense oligonucleotide according to claim 1.

15. A kit to treat or ameliorate the effects of a disease associated with VEGF-A in a subject, which kit comprises at least the antisense oligonucleotide according to claim 1, packaged in a suitable container, together with instructions for its use.

16. The kit of claim 15 wherein the disease associated with VEGF-A is a solid tumour cancer, aged-related macular degeneration, diabetic retinopathy, rheumatoid arthritis or diabetic macular edema.

* * * * *